United States Patent
Noureldin et al.

(10) Patent No.: US 9,803,507 B2
(45) Date of Patent: Oct. 31, 2017

(54) POWER GENERATION USING INDEPENDENT DUAL ORGANIC RANKINE CYCLES FROM WASTE HEAT SYSTEMS IN DIESEL HYDROTREATING-HYDROCRACKING AND CONTINUOUS-CATALYTIC-CRACKING-AROMATICS FACILITIES

(71) Applicant: Saudi Arabian Oil Company, Dhahran (SA)

(72) Inventors: Mahmoud Bahy Mahmoud Noureldin, Dhahran (SA); Hani Mohammed Al Saed, Jubail Ind. (SA); Ahmad Saleh Bunaiyan, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/087,440

(22) Filed: Mar. 31, 2016

(65) Prior Publication Data

US 2017/0058706 A1 Mar. 2, 2017

Related U.S. Application Data

(60) Provisional application No. 62/209,217, filed on Aug. 24, 2015, provisional application No. 62/209,147, (Continued)

(51) Int. Cl.
*F01K 13/02* (2006.01)
*C10G 69/00* (2006.01)
(Continued)

(52) U.S. Cl.
CPC ............ *F01K 13/02* (2013.01); *C07C 5/2732* (2013.01); *C07C 7/00* (2013.01); *C10G 53/04* (2013.01);
(Continued)

(58) Field of Classification Search
CPC . F01K 13/02; F01K 3/185; F01K 3/00; F01K 27/00; C10G 57/00; C10G 55/00; C10G 53/04; C10G 69/00
See application file for complete search history.

(56) References Cited

U.S. PATENT DOCUMENTS 3,995,428 A 12/1976 Roberts
4,024,908 A 5/1977 Meckler
(Continued)

FOREIGN PATENT DOCUMENTS

CN 1844325 10/2006
CN 101424453 5/2009
(Continued)

OTHER PUBLICATIONS

PCT International Search Report and Written Opinion of the International Searching Authority, PCT/US2016/048210, Dec. 22, 2016, 11 pages.
(Continued)

*Primary Examiner* — Viet Nguyen
(74) *Attorney, Agent, or Firm* — Fish & Richardson P.C.

(57) ABSTRACT

Optimizing power generation from waste heat in large industrial facilities such as petroleum refineries by utilizing a subset of all available hot source streams selected based, in part, on considerations for example, capital cost, ease of operation, economics of scale power generation, a number of organic Rankine cycle (ORC) machines to be operated, operating conditions of each ORC machine, combinations of them, or other considerations are described. Subsets of hot sources that are optimized to provide waste heat to one or more ORC machines for power generation are also described. Further, recognizing that the utilization of waste heat from all available hot sources in a mega-site such as a petroleum refinery and aromatics complex is not necessarily or not always the best option, hot source units in petroleum (Continued)

refineries from which waste heat can be consolidated to power the one or more ORC machines are identified.

24 Claims, 23 Drawing Sheets

Related U.S. Application Data filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| *F01D 17/14* | (2006.01) | |
| *F01K 3/18* | (2006.01) | |
| *H02K 7/18* | (2006.01) | |
| *C10G 59/00* | (2006.01) | |
| *C10G 61/00* | (2006.01) | |
| *C10G 63/00* | (2006.01) | |
| *F01K 3/00* | (2006.01) | |
| *F01K 27/00* | (2006.01) | |
| *C10G 53/04* | (2006.01) | |
| *C10G 55/00* | (2006.01) | |
| *C10G 57/00* | (2006.01) | |
| *C10G 61/10* | (2006.01) | |
| *C07C 5/27* | (2006.01) | |
| *C07C 7/00* | (2006.01) | |

(52) U.S. Cl.
CPC .............. *C10G 55/00* (2013.01); *C10G 57/00* (2013.01); *C10G 59/00* (2013.01); *C10G 61/00* (2013.01); *C10G 61/10* (2013.01); *C10G 63/00* (2013.01); *C10G 69/00* (2013.01); *F01D 17/145* (2013.01); *F01K 3/00* (2013.01); *F01K 3/185* (2013.01); *F01K 27/00* (2013.01); *H02K 7/1823* (2013.01); *C10G 2300/4006* (2013.01); *C10G 2400/04* (2013.01); *C10G 2400/30* (2013.01)

(56) References Cited

U.S. PATENT DOCUMENTS

| | | | |
|---|---|---|---|
| 4,109,469 A | 8/1978 | Carson | |
| 4,291,232 A | 9/1981 | Cardone | |
| 4,428,201 A | 1/1984 | Carson | |
| 4,471,619 A | 9/1984 | Nolley, Jr. | |
| 4,476,680 A | 10/1984 | Pollman | |
| 4,512,155 A | 4/1985 | Sheinbaum | |
| 4,792,390 A | 12/1988 | Staggs | |
| 4,962,238 A | 10/1990 | Wolfe | |
| 5,005,360 A | 4/1991 | McMurtry | |
| 5,007,240 A | 4/1991 | Ishida | |
| 5,164,070 A * | 11/1992 | Munro | C10G 49/22 |
| | | | 208/100 |
| 5,240,476 A | 8/1993 | Hegarty | |
| 5,497,624 A | 3/1996 | Amir | |
| 5,562,190 A | 10/1996 | McArthur | |
| 5,667,051 A | 9/1997 | Goldberg | |
| 5,685,152 A | 11/1997 | Sterling | |
| 5,740,677 A | 4/1998 | Vestesen | |
| 5,804,060 A * | 9/1998 | Benguigui | C10G 21/003 |
| | | | 196/14.52 |
| 6,041,849 A | 3/2000 | Karl | |
| 6,733,636 B1 | 5/2004 | Heins | |
| 7,340,899 B1 | 3/2008 | Rubak | |
| 8,046,999 B2 | 11/2011 | Doty | |
| 8,529,202 B2 | 9/2013 | Zhang | |
| 9,328,634 B2 | 5/2016 | Ikegami | |
| 9,334,760 B2 | 5/2016 | Ernst | |
| 9,518,497 B2 | 12/2016 | Tricaud | |
| 9,562,201 B2 | 2/2017 | Noureldin | |
| 2006/0010872 A1 | 1/2006 | Singh | |
| 2008/0128134 A1 | 6/2008 | Mudunuri | |
| 2008/0174115 A1 * | 7/2008 | Lambirth | E21B 36/04 |
| | | | 290/2 |
| 2008/0289588 A1 | 11/2008 | Wees et al. | |
| 2008/0307789 A1 | 12/2008 | Mak | |
| 2008/0314726 A1 | 12/2008 | Choros | |
| 2009/0000299 A1 | 1/2009 | Ast | |
| 2009/0000906 A1 | 1/2009 | Petri | |
| 2009/0071652 A1 | 3/2009 | Vinegar | |
| 2009/0225929 A1 | 9/2009 | Genta et al. | |
| 2009/0287029 A1 | 11/2009 | Anumakonda et al. | |
| 2009/0301087 A1 | 12/2009 | Borissov et al. | |
| 2010/0076238 A1 | 3/2010 | Brandvold | |
| 2010/0146974 A1 | 6/2010 | Ast | |
| 2010/0242476 A1 | 9/2010 | Ast | |
| 2010/0263380 A1 | 10/2010 | Biederman | |
| 2010/0319346 A1 | 12/2010 | Ast | |
| 2010/0326076 A1 | 12/2010 | Ast | |
| 2010/0326098 A1 | 12/2010 | Rog | |
| 2011/0016863 A1 | 1/2011 | Ernst | |
| 2011/0041500 A1 | 2/2011 | Riley | |
| 2011/0072819 A1 | 3/2011 | Silva et al. | |
| 2011/0072820 A1 | 3/2011 | Finkenrath | |
| 2011/0083437 A1 | 4/2011 | Ast | |
| 2011/0158858 A1 | 6/2011 | Alves Ramalho Gomes | |
| 2011/0203289 A1 * | 8/2011 | Gutierrez | F01K 23/068 |
| | | | 60/772 |
| 2011/0314844 A1 | 12/2011 | Gu et al. | |
| 2012/0000175 A1 | 1/2012 | Wormser | |
| 2012/0031096 A1 * | 2/2012 | Ulas Acikgoz | F01K 25/08 |
| | | | 60/651 |
| 2012/0047889 A1 | 3/2012 | Ulas Acikgoz et al. | |
| 2012/0085095 A1 | 4/2012 | Penton et al. | |
| 2012/0085096 A1 | 4/2012 | Penton et al. | |
| 2012/0085097 A1 | 4/2012 | Penton et al. | |
| 2012/0087783 A1 | 4/2012 | Zhang | |
| 2012/0131921 A1 | 5/2012 | Held | |
| 2012/0145050 A1 | 6/2012 | Fisenko | |
| 2012/0192563 A1 | 8/2012 | Kauffman | |
| 2012/0198768 A1 | 8/2012 | Khosravian | |
| 2012/0204817 A1 * | 8/2012 | Scherffius | B01D 3/322 |
| | | | 122/7 R |
| 2012/0234263 A1 | 9/2012 | Van Wees et al. | |
| 2012/0279728 A1 | 11/2012 | Northrop | |
| 2012/0279900 A1 | 11/2012 | Noureldin et al. | |
| 2012/0285169 A1 | 11/2012 | Freund | |
| 2013/0047574 A1 * | 2/2013 | Kidambi | C01B 17/0404 |
| | | | 60/39.12 |
| 2013/0062883 A1 | 3/2013 | Kaneeda | |
| 2013/0090395 A1 | 4/2013 | DiGenova et al. | |
| 2013/0091843 A1 | 4/2013 | Zyhowski et al. | |
| 2013/0104546 A1 | 5/2013 | Goswami | |
| 2013/0145763 A1 | 6/2013 | Mirmobin et al. | |
| 2013/0165534 A1 | 6/2013 | McComish | |
| 2013/0213040 A1 | 8/2013 | Goswami | |
| 2013/0231909 A1 | 9/2013 | Noureldin | |
| 2013/0238154 A1 | 9/2013 | Noureldin | |
| 2013/0291808 A1 | 11/2013 | Kautto | |
| 2013/0334060 A1 | 12/2013 | Koseoglu et al. | |
| 2014/0090405 A1 | 4/2014 | Held et al. | |
| 2014/0174084 A1 | 6/2014 | Kontomaris | |
| 2014/0260311 A1 | 9/2014 | Berlowitz | |
| 2014/0318124 A1 * | 10/2014 | Ernst | F01N 5/02 |
| | | | 60/618 |
| 2015/0027118 A1 | 1/2015 | Tricaud | |
| 2015/0073188 A1 * | 3/2015 | Floudas | C10G 35/00 |
| | | | 585/332 |
| 2015/0361831 A1 | 12/2015 | Myers | |
| 2015/0377079 A1 | 12/2015 | Noureldin | |
| 2016/0032786 A1 * | 2/2016 | Zampieri | F01K 13/02 |
| | | | 60/670 |
| 2016/0045841 A1 | 2/2016 | Kaplan | |
| 2016/0076347 A1 | 3/2016 | Diez | |
| 2017/0058202 A1 | 3/2017 | Noureldin | |
| 2017/0058703 A1 | 3/2017 | Noureldin | |
| 2017/0058704 A1 * | 3/2017 | Noureldin | C10G 57/00 |

(56) References Cited

U.S. PATENT DOCUMENTS

| | | | |
|---|---|---|---|
| 2017/0058705 A1 | 3/2017 | Noureldin | |
| 2017/0058706 A1 | 3/2017 | Noureldin | |
| 2017/0058708 A1 | 3/2017 | Noureldin | |
| 2017/0058709 A1 | 3/2017 | Noureldin | |
| 2017/0058711 A1 | 3/2017 | Noureldin | |
| 2017/0058713 A1 | 3/2017 | Noureldin | |
| 2017/0058714 A1* | 3/2017 | Noureldin | C10G 45/02 |
| 2017/0058718 A1 | 3/2017 | Noureldin | |
| 2017/0058719 A1 | 3/2017 | Noureldin | |
| 2017/0058720 A1* | 3/2017 | Noureldin | C10G 45/02 |
| 2017/0058721 A1 | 3/2017 | Noureldin | |
| 2017/0058722 A1 | 3/2017 | Noureldin | |
| 2017/0058723 A1* | 3/2017 | Noureldin | C10G 45/02 |

FOREIGN PATENT DOCUMENTS

| | | |
|---|---|---|
| CN | 104560082 | 4/2015 |
| DE | 3731978 | 3/1988 |
| EP | 0292391 | 11/1988 |
| EP | 949318 | 10/1999 |
| EP | 2516326 | 10/2012 |
| FR | 2990990 | 11/2013 |
| SU | 295317 | 10/1977 |
| WO | 97/21786 | 6/1997 |
| WO | 2004102082 | 11/2004 |
| WO | 2011090553 | 7/2011 |
| WO | WO2012048132 A2 | 4/2012 |
| WO | WO2013055864 A1 | 4/2013 |
| WO | 2014205163 | 12/2014 |

OTHER PUBLICATIONS

PCT International Search Report and Written Opinion of the International Searching Authority, PCT/US2016/048224, Dec. 22, 2016, 11 pages.
PCT International Search Report and Written Opinion of the International Searching Authority, PCT/US2016/048209, Dec. 22, 2016, 11 pages.
PCT International Search Report and Written Opinion of the International Searching Authority, PCT/US2016/048237, Dec. 22, 2016, 11 pages.
PCT International Search Report and Written Opinion of the International Searching Authority, PCT/US2016/048223, Dec. 22, 2016, 11 pages.
PCT International Search Report and Written Opinion of the International Searching Authority, PCT/US2016/048212, Dec. 22, 2016, 11 pages.
Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.
Stecco, "Kalina Cycles: Some Possible Applications and Comments," Proceedings of the American Power Conference, XP 000609703, Jan. 1, 1993, vol. 1, pp. 196-201.
Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-223.
Sadrameli et al., "Optimum Operating Conditions for a Combined Power and Cooling Thermodynamic Cycle," Science Direct, Applied Energy, vol. 84, No. 3, Nov. 10, 2006, pp. 254-265.
Vidal, "Analysis of a Combined Power and Refrigeration Cycle by the Exergy Method," Science Direct, Energy 31, Dec. 1, 2006, pp. 3401-3414.
PCT International Search Report and Written Opinion of the International Searching Authority, PCT/US2016/027417, Jul. 6, 2016, 11 pages.
PCT International Search Report and Written Opinion of the International Searching Authority, PCT/US2016/027797, Oct. 19, 2016, 12 pages.
PCT International Search Report and Written Opinion of the International Searching Authority, PCT/US2016/027794, Oct. 19, 2016, 13 pages.
PCT International Search Report and Written Opinion of the International Searching Authority, PCT/US2016/030063, Oct. 19, 2016, 13 pages.
PCT International Search Report and Written Opinion of the International Searching Authority, PCT/US2016/030156, Oct. 19, 2016, 12 pages.
PCT International Search Report and Written Opinion of the International Searching Authority, PCT/US2016/048074, Nov. 9, 2016, 12 pages.
PCT International Search Report and Written Opinion of the International Searching Authority, PCT/US2016/048042, Nov. 9, 2016, 12 pages.
PCT International Search Report and Written Opinion of the International Searching Authority, PCT/US2016/048219, Nov. 21, 2016, 13 pages.
PCT International Search Report and Written Opinion of the International Searching Authority, PCT/US2016/048229, Nov. 21, 2016, 13 pages.
PCT International Search Report and Written Opinion of the International Searching Authority, PCT/US2016/048236, Nov. 21, 2016, 13 pages.
PCT International Search Report and Written Opinion of the International Searching Authority, PCT/US2016/048067, Nov. 15, 2016, 11 pages.
PCT International Search Report and Written Opinion of the International Searching Authority, PCT/US2016/048066, Nov. 15, 2016, 11 pages.
PCT International Search Report and Written Opinion of the International Searching Authority, PCT/US2016/048078, Nov. 15, 2016, 12 pages.
PCT International Search Report and Written Opinion of the International Searching Authority, PCT/US2016/048076, Nov. 15, 2016, 12 pages.
PCT International Search Report and Written Opinion of the International Searching Authority, PCT/US2016/048207, Nov. 21, 2016, 12 pages.
PCT International Search Report and Written Opinion of the International Searching Authority, PCT/US2016/027413, Nov. 22, 2016, 11 pages.
PCT International Search Report and Written Opinion of the International Searching Authority, PCT/US2016/048063, Nov. 23, 2016, 11 pages.
PCT International Search Report and Written Opinion of the International Searching Authority, PCT/US2016/048071, Nov. 23, 2016, 11 pages.
"Organic Rankine Cycle," Choice of the Working Fluid, Wikipedia, published on or before Sep. 2014, 4 pages. http://en.wikipedia.org/wiki/Organic_Rankine_cycle?oldid=628773207.
Bourji et al., "Optimizing an Organic Rankine Cycle," CEP—Chemical Engineering Progress, Jan. 2013, 6 pages.
Handayani et al., "Opportunities for Organic Rankine Cycles (ORCs) in the Process Industries," Newcastle University, Oct. 25-26, 2011, 40 pages.
Kapil et al., "Advanced Process Integration for Low Grade Heat Recovery," published on or before Mar. 2010, 58 pages.
Meacher, Organic Rankine Cycle Systems for Waste Heat Recovery in Refineries and Chemical Process Plants, Proceedings from the Third Industrial Energy Technology Conference Houston, TX, Apr. 26-29, 1981, 8 pages.
Rowshanaie et al., "Generating the Electricity from Fluegas Produced by Boiler through a ORC Thermodynamic Cycle (Organic Rankine Cycle) by using a Shaft Tightness in Turbo-Expander," International Conference on Chemical, Agricultural and Medical Sciences, Dec. 29-30, 2013, 4 pages.
Tillman, "Low Temperature Waste Energy Recovery in Chemical Plants and Refineries," TAS Energy Inc., May 16, 2012, 11 pages.
Bertrand F. Tchanche, Gr. Lambrinos, A. Frangoudakis and G. Papadakis "Low-grade heat conversion into power using organic Rankine cycles—A review of various applications", Renewable and

(56) References Cited

OTHER PUBLICATIONS

Sustainable Energy Reviews, 15 (2011) 3963-3979 (abstract provided, full article can be provided upon request).

Jung et al., "Feasibility assessment of refinery waste heat to power conversion using an organic Rankine cycle", Energy conversion and Management, vol. 77, published in 2014, pp. 396-407.

Jose Maria Ponce-Ortega, et al., "Optimal design of inter-plant waste energy integration", Applied Thermal Engineering, 62 (2014), 633-652 (abstract provided, full article can be provided upon request).

Kevin J.DiGenova, Barbara B.Botros, and J.G. Brisson, "Method for customizing an organic Rankine cycle to a aomplex heat source for efficient energy conversion, demonstrated on a Fischer Tropsch plant", Applied energy, 102 (2013), 746-754 (abstract provided, full article can be provided upon request).

* cited by examiner

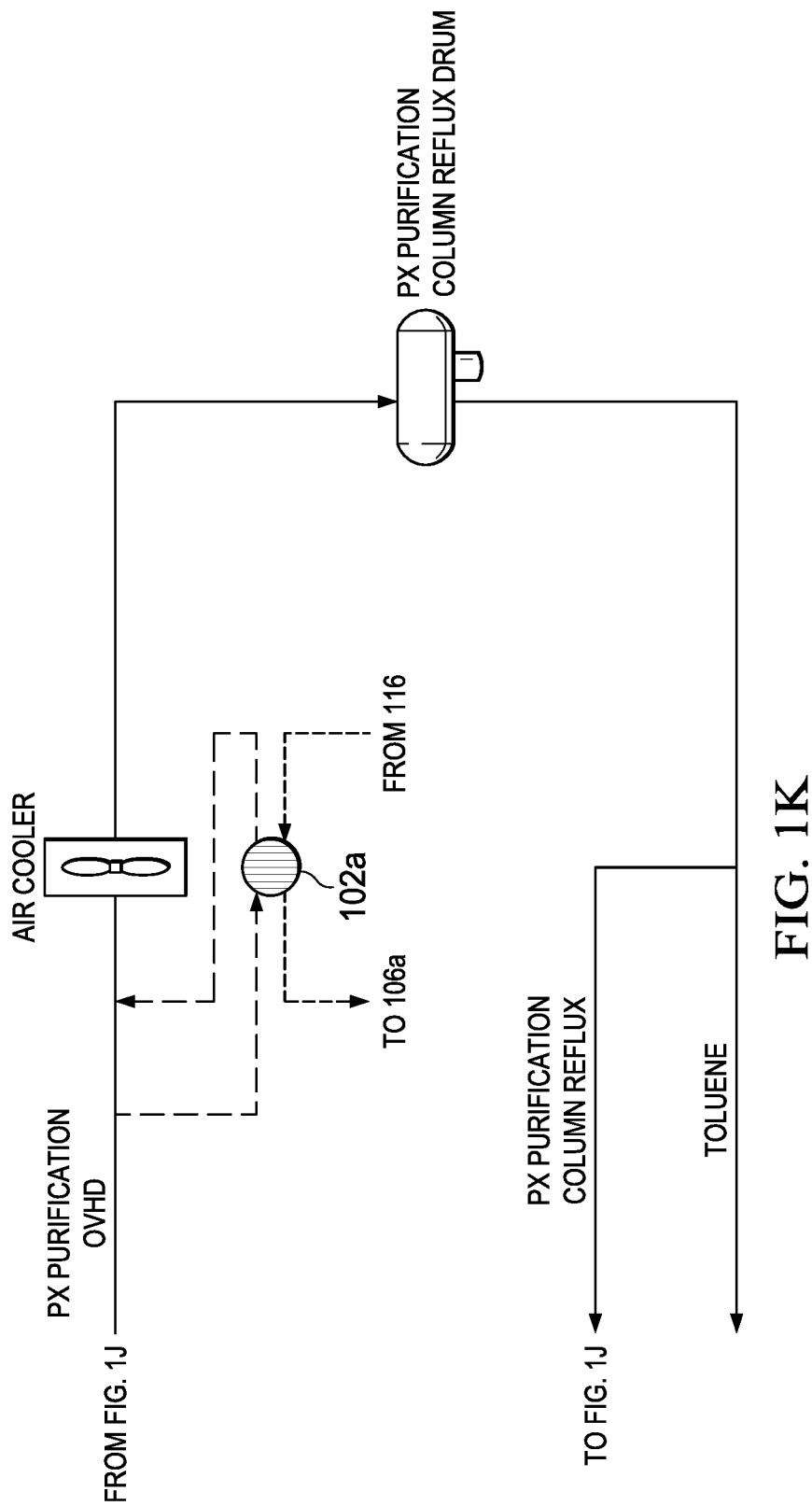

POWER GENERATION USING INDEPENDENT DUAL ORGANIC RANKINE CYCLES FROM WASTE HEAT SYSTEMS IN DIESEL HYDROTREATING-HYDROCRACKING AND CONTINUOUS-CATALYTIC-CRACKING-AROMATICS FACILITIES

CROSS-REFERENCE TO RELATED APPLICATION

This application claims priority under 35 U.S.C. §119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to power generation in industrial facilities.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be re-used, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to power generation from waste energy in industrial facilities. The present disclosure includes one or more of the following units of measure with their corresponding abbreviations, as shown in Table 1:

TABLE 1

| Unit of Measure | Abbreviation |
| --- | --- |
| Degrees Celsius | ° C. |
| Megawatts | MW |
| One million | MM |
| British thermal unit | Btu |
| Hour | h |
| Pounds per square inch (pressure) | psi |
| Kilogram (mass) | Kg |
| Second | S |

The details of one or more implementations of the subject matter described in this specification are set forth in the accompanying drawings and the description later. Other features, aspects, and advantages of the subject matter will become apparent from the description, the drawings, and the claims.

DETAILED DESCRIPTION

Figure 1A:
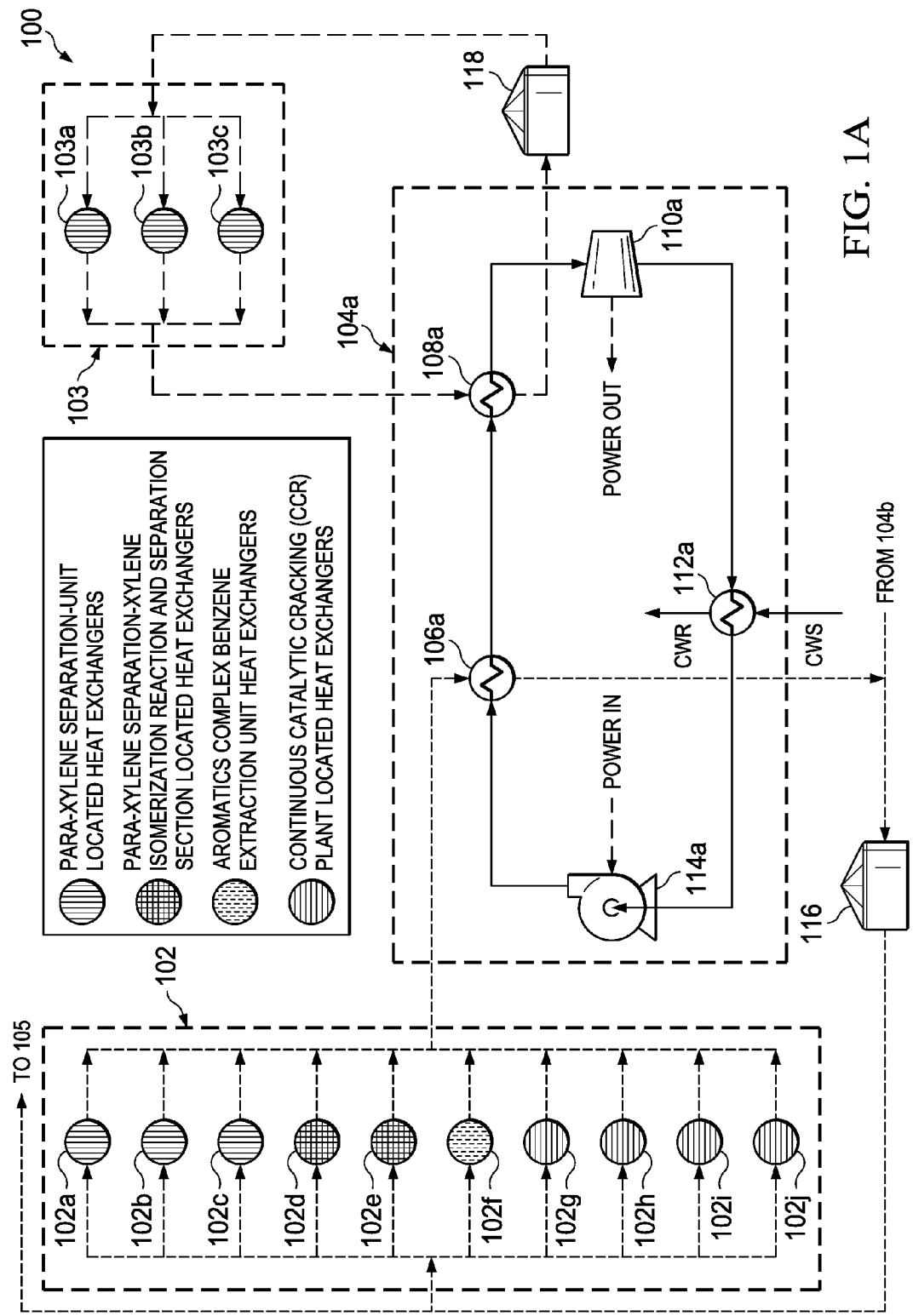
FIGS. 1A-1T are schematic illustrations of a power generation system that utilizes waste heat from one or more heat sources in a petrochemical refining plant.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM Btu/h can be wasted to a network of air coolers extended along the crude oil and aromatics site. Some of the wasted heat can be used to power an Organic Rankine Cycle (ORC) machine, which uses an organic fluid such as refrigerants or hydrocarbons (or both) instead of water to generate power. ORC machines in combination with low temperature heat sources (for example, about 232° C. or less) are being implemented as power generation systems. Optimizing ORC machines, for example, by optimizing the power generation cycle (that is, the Rankine cycle) or the organic fluid implemented by the ORC machine (or both), can improve power generation from recovered waste heat.

An industrial facility such as a petroleum refinery includes several sources of waste heat. One or more ORC machines can receive the waste heat from one or more or all of such sources. In some implementations, two or more sources of low grade heat can be consolidated by transferring heat from each of the sources to a common intermediate heat transfer medium (for example, water or other fluid). The intermediate heat transfer medium can then be used to evaporate the working fluid of the ORC machine to generate power, for example, to operate a turbine or other power generator. Such consolidation of sources of low grade heat can allow the ORC machine to be sized to realize greater efficiencies and economies of scale. Further, such a consolidated operation can improve flexibility in petroleum refinery design and plot space planning, since each heat source need not be in close proximity to the power generator. The proposed consolidation of heat sources, particularly, in mega sites such as a site-wide oil refinery that includes an aromatics complex and is the size of an eco-industrial park can represent an over-simplification of the problem of improving the process of recovering waste heat to generate power.

This disclosure describes optimizing power generation from waste heat, for example, low grade heat at a temperature at or less than 160° C. in large industrial facilities (for example, petroleum refineries or other large industrial refineries with several, sometimes more than 50, hot source streams) by utilizing a subset of all available hot source streams selected based, in part, on considerations for example, capital cost, ease of operation, economics of scale power generation, a number of ORC machines to be operated, operating conditions of each ORC machine, combinations of them, or other considerations. Recognizing that several subsets of hot sources can be identified from among the available hot sources in a large petroleum refinery, this disclosure describes selecting subsets of hot sources that are optimized to provide waste heat to one or more ORC machines for power generation. Further, recognizing that the utilization of waste heat from all available hot sources in a mega-site such as a petroleum refinery and aromatics complex is not necessarily or not always the best option, this disclosure identifies hot source units in petroleum refineries from which waste heat can be consolidated to power the one or more ORC machines.

This disclosure also describes modifying medium grade crude oil refining semi-conversion facilities and integrated medium grade crude oil refining semi-conversion and aromatics facilities plants' designs to improve their energy efficiencies relative to their current designs. To do so, new facilities can be designed or existing facilities can be re-designed (for example, retro-fitted with equipment) to recover waste heat, for example, low grade waste heat, from heat sources to power ORC machines. In particular, the existing design of a plant need not be significantly altered to accommodate the power generation techniques described here. The generated power can be used, in part, to power the facilities or transported to the electricity grid to be delivered elsewhere (or both).

By recovering all or part of the waste heat generated by one or more processes or facilities (or both) of industrial facilities and converting the recovered waste heat into power, carbon-free power (for example, in the form of electricity) can be generated for use by the community. The minimum approach temperature used in the waste heat recovery processes can be as low as 3° C. and the generated power can be as high as 80 MW. In some implementations, higher minimum approach temperatures can be used in an initial phase at the expense of less waste heat/energy recovery, while relatively better power generation (for example, in terms of economy of scale design and efficiency) is realized in a subsequent phase upon using the minimum approach temperature for the specific hot sources uses. In such situations, more power generation can be realized in the subsequent phase without needing to change the design topology of the initial phase or the subset of the low grade waste hot sources used in the initial phase (or both).

Not only pollution associated but also cost associated with power generation can be decreased. In addition, recovering waste heat from a customized group of hot sources to power one or more ORC machines is more optimal than recovering waste heat from all available hot sources. Selecting the hot sources in the customized group instead of or in addition to optimizing the ORC machine can improve or optimize (or both) the process of generating power from recovered waste heat. If a few number of hot sources are used for power generation, then the hot sources can be consolidated into few (for example, one or two) buffer streams using fluids, for example, hot oil or high pressure hot water system, or a mixture of the two.

In sum, this disclosure describes several petroleum refinery-wide separation/distillation networks, configurations, and processing schemes for efficient power generation using a basic ORC machine operating under specified conditions. The power generation is facilitated by obtaining all or part of waste heat, for example, low grade waste heat, carried by multiple, scattered low grade energy quality process streams. In some implementations, the ORC machine uses separate organic material to pre-heat the exchanger and evaporator and uses other organic fluid, for example, isobutane, at specific operating conditions.

Examples of Petroleum Refinery Plants

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM Btu/h can be wasted to a network of air coolers extended along the crude oil and aromatics site. Some of the wasted heat can be used to power an Organic Rankine Cycle (ORC) machine, which uses an organic fluid such as refrigerants or hydrocarbons (or both) instead of water to generate power. ORC machines in combination with low temperature heat sources (for example, about or less than 232° C.) are being implemented as power generation systems. Optimizing ORC machines, for example, by optimizing the power generation cycle (that is, the Rankine cycle) or the organic fluid implemented by the ORC machine (or both), can improve power generation from recovered waste heat.

An industrial facility such as a petroleum refinery includes several sources of waste heat. One or more ORC machines can receive the waste heat from one or more or all of such sources. In some implementations, two or more sources of low grade heat can be consolidated by transferring heat from each of the sources to a common intermediate heat transfer medium (for example, water or other fluid). The intermediate heat transfer medium can then be used to evaporate the working fluid of the ORC machine to generate power, for example, to operate a turbine or other power generator. Such consolidation of sources of low grade heat can allow the ORC machine to be sized to realize greater efficiencies and economies of scale. Further, such a consolidated operation can improve flexibility in petroleum refinery design and plot space planning, since each heat source need not be in close proximity to the power generator. The proposed consolidation of heat sources, particularly, in mega sites such as a site-wide oil refinery that includes an aromatics complex and is the size of an eco-industrial park can represent an over-simplification of the problem of improving the process of recovering waste heat to generate power.

This disclosure describes optimizing power generation from waste heat, for example, low grade heat at a temperature at or less than 160° C. in large industrial facilities (for example, petroleum refineries or other large industrial refineries with several, sometimes more than 50, hot source streams) by utilizing a subset of all available hot source streams selected based, in part, on considerations for example, capital cost, ease of operation, economics of scale power generation, a number of ORC machines to be operated, operating conditions of each ORC machine, combinations of them, or other considerations. Recognizing that several subsets of hot sources can be identified from among the available hot sources in a large petroleum refinery, this disclosure describes selecting subsets of hot sources that are optimized to provide waste heat to one or more ORC machines for power generation. Further, recognizing that the utilization of waste heat from all available hot sources in a mega-site such as a petroleum refinery and aromatics complex is not necessarily or not always the best option, this disclosure identifies hot source units in petroleum refineries from which waste heat can be consolidated to power the one or more ORC machines.

This disclosure also describes modifying medium grade crude oil refining semi-conversion facilities and integrated medium grade crude oil refining semi-conversion and aromatics facilities plants' designs to improve their energy efficiencies relative to their current designs. To do so, new facilities can be designed or existing facilities can be re-designed (for example, retro-fitted with equipment) to recover waste heat, for example, low grade waste heat, from heat sources to power ORC machines. In particular, the existing design of a plant need not be significantly altered to accommodate the power generation techniques described here. The generated power can be used, in part, to power the facilities or transported to the electricity grid to be delivered elsewhere (or both).

By recovering all or part of the waste heat generated by one or more processes or facilities of industrial facilities (or both) and converting the recovered waste heat into power, carbon-free power (for example, in the form of electricity) can be generated for use by the community. The minimum approach temperature used in the waste heat recovery processes can be as low as 3° C. and the generated power can be as high as 80 MW. In some implementations, higher minimum approach temperatures can be used in an initial phase at the expense of less waste heat/energy recovery, while relatively better power generation (for example, in terms of economy of scale design and efficiency) is realized in a subsequent phase upon using the minimum approach temperature for the specific hot sources uses. In such situations, more power generation can be realized in the subsequent phase without needing to change the design topology of the initial phase or the subset of the low grade waste hot sources used in the initial phase (or both).

Not only pollution associated but also cost associated with power generation can be decreased. In addition, recovering waste heat from a customized group of hot sources to power one or more ORC machines is more cost effective from a capital cost point-of-view than recovering waste heat from all available hot sources. Selecting the hot sources in the customized group instead of or in addition to optimizing the ORC machine can improve or optimize the process of generating power from recovered waste heat (or both). If a few number of hot sources are used for power generation, then the hot sources can be consolidated into few (for example, one or two) buffer streams using fluids, for example, hot oil or high pressure hot water system (or both).

In sum, this disclosure describes several petroleum refinery-wide separation/distillation networks, configurations, and processing schemes for efficient power generation using a basic ORC machine operating under specified conditions. The power generation is facilitated by obtaining all or part of waste heat, for example, low grade waste heat, carried by multiple, scattered low grade energy quality process streams. In some implementations, the ORC machine uses separate organic material to pre-heat the exchanger and evaporator and uses other organic fluid, for example, isobutane, at specific operating conditions.

Examples of Petroleum Refinery Plants

1. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromatic content or high concentrations of the two principal catalyst poisons, sulfur and nitrogen compounds (or both).

The hydrocracking process depends on the nature of the feedstock and the relative rates of the two competing reactions, hydrogenation and cracking. Heavy aromatic feedstock is converted into lighter products under a wide range of high pressures and high temperatures in the presence of hydrogen and special catalysts. When the feedstock has a high paraffinic content, hydrogen prevents the formation of polycyclic aromatic compounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces isobutane for alkylation feedstock, and also performs isomerization for pour-point control and smoke-point control, both of which are important in high-quality jet fuel.

2. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

3. Aromatics Complex

A typical aromatics complex includes a combination of process units for the production of basic petrochemical intermediates of benzene, toluene and xylenes (BTX) using the catalytic reforming of naphtha using continuous catalyst regeneration (CCR) technology.

4. Naphtha Hydrotreating Plant and Continuous Catalytic Reformer Plants

A Naphtha Hydrotreater (NHT) produces 101 Research Octane Number (RON) reformate, with a maximum 4.0 psi Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the continuous catalyst regeneration (CCR) platformer and gasoline blending.

5. Crude Distillation Plant

Normally, a two-stage distillation plant processes various crude oils that are fractionated into different products, which are further processed in downstream facilities to produce liquefied petroleum gas (LPG), Naphtha, Motor Gasoline, Kerosene, Jet Fuel, Diesel, Fuel Oil and Asphalt. The Crude Distillation plant can typically process large volumes, for example, hundreds of thousands of barrels, of crude oil per day. During the summer months the optimum processing capacity may decrease. The plant can process mixture of crudes. The plant can also have asphalt producing facilities. The products from crude distillation plant are LPG, stabilized whole naphtha, kerosene, diesel, heavy diesel, and vacuum residuum. The Atmospheric Column receives the crude charge and separates it into overhead product, kerosene, diesel, and reduced crude. The Naphtha stabilizer may receive the atmospheric overhead stream and separates it into LPG and stabilized naphtha. The reduced crude is charged to the Vacuum tower where it is further separated into heavy diesel, vacuum gas oils and vacuum residuum.

6. Sour Water Stripping Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

One of more of the refinery plants described earlier can supply heat, for example, in the form of low grade waste heat, to the ORC machine with reasonable economics of scale, for example, tens of megawatts of power. Studies have shown that particular refinery plants, for example, a hydrocracking plant, serve as good waste heat sources to generate power. However, in a study using only the hot source from the naphtha hydrotreating (NHT) plant, for example, at about 111° C., 1.7 MW of power was produced from about 27.6 MW of available waste heat at a low efficiency of about 6.2%. The low efficiency suggests that a hot source from the NHT plant alone is not recommended for waste heat generation due to high capital and economy of scale. In another study using one low grade hot source at about 97° C. from a crude distillation plant, 3.5 MW of power was produced from about 64.4 MW of available waste heat at a low efficiency of 5.3%. In a further study using one low grade hot source at about 120° C. from a sour water stripping plant, 2.2 MW of power was produced from about 32.7 MW of available waste heat at a low efficiency of 6.7%. These studies reveal that if waste heat recovery from a particular refinery plant to generate power is determined to be beneficial, it does not necessarily follow that waste heat recovery from any refinery plant will also be beneficial.

In another study, all waste heat available from all hot sources (totaling 11 hot source streams) in an aromatics complex were collected to generate about 13 MW of power from about 241 MW of available waste heat. This study reveals that using all available hot sources, while theoretically efficient, does not, in practice, necessarily translate to efficient power generation from available waste heat. Moreover, assembling power plants that can use all available hot sources can be very difficult considering the quantity of heat exchangers, pumps, and organic-based turbines (among other components and inter-connectors) involved. Not only will it be difficult to retrofit existing refineries to accommodate such power plants, but it will also be difficult to build such power plants from a grass roots stage. In the following sections, this disclosure describes combinations of hot sources selected from different refinery plants which can result in high efficiencies in generating power from available waste heat.

Even after identifying specific hot sources to be used for power generation in a mega-size site, there can be several combinations of hot sources that can be integrated for optimum generation of power using a specific ORC machine operating under specific conditions. Each of the following sections describes a specific combination of hot sources and a configuration for buffer systems which can be implemented with the specific combination to optimally generate power from waste heat with as minimum capital utilization as necessary. Also, the following sections describe two-buffer systems for low grade waste heat recovery where one-buffer systems for waste heat recovery as inapplicable. Each section describes the interconnections and related processing schemes between the different plants that make up the specific combination of hot sources, the configurations including components such as heat exchangers added in specific plants, at specific places and to specific streams in the process to optimize waste heat recovery and power generation. As described later, the different configurations can be implemented without changing the current layout or processes implemented by the different plants. The new configurations described in the sections later can generate between about 34 MW and about 80 MW of power from waste heat, enabling a proportional decrease of GHG emissions in petroleum refineries. The configurations described in the sections later demonstrate more than one way to achieve desired energy recovery using buffer systems. The configurations are related processing schemes do not impact and can be integrated with future potential in-plant energy saving initiatives, for example, low pressure steam generation. The configurations and processing schemes can render more than 10% first law efficiency for power generation from the low grade waste heat into the ORC machine.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, in other words, the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

Figure 1B:
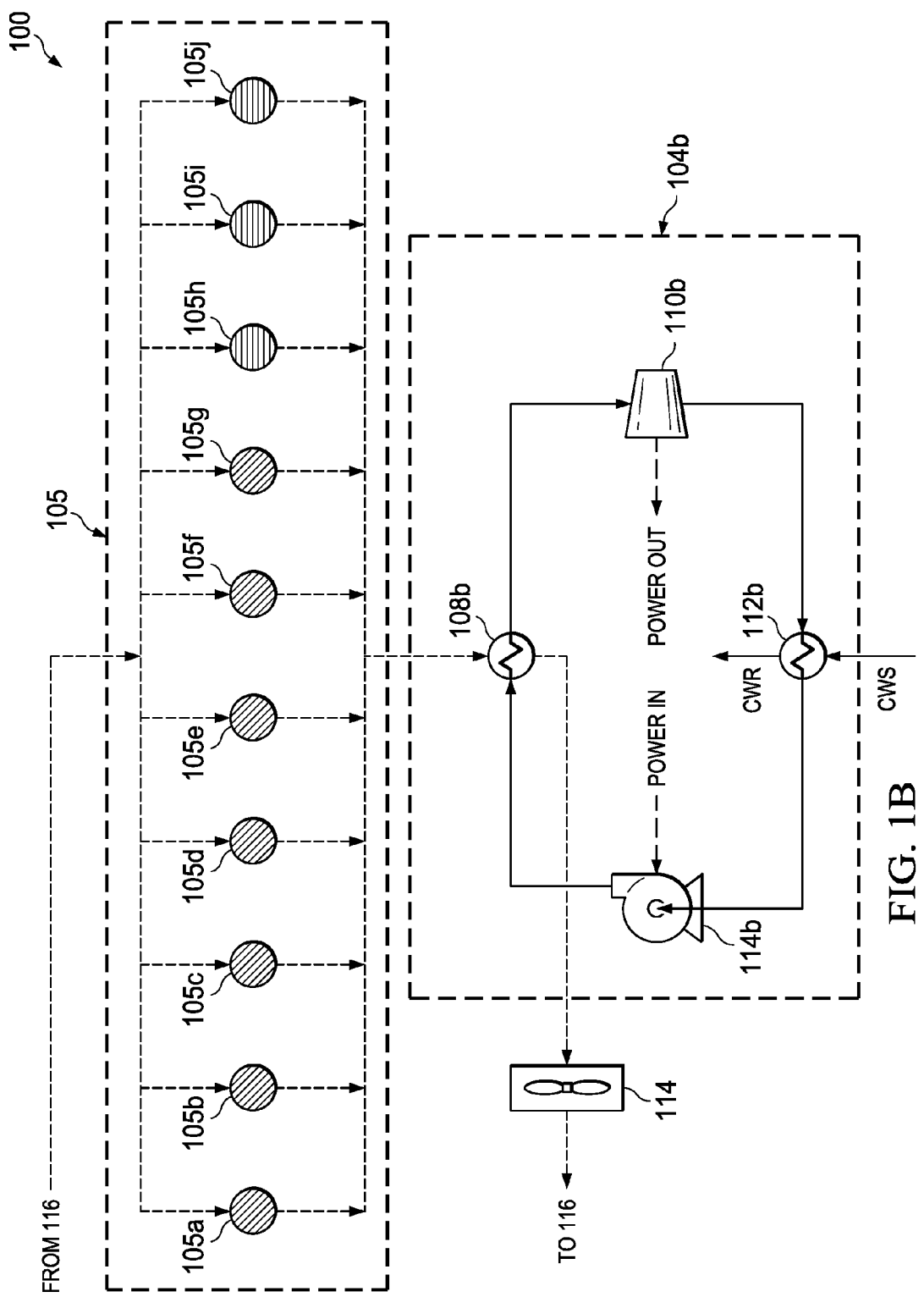
FIGS. 1U-1X are graphs that illustrate heat exchanger performance of heat exchangers in the power generation system shown in FIGS. 1S-1T.
Figure 1C:
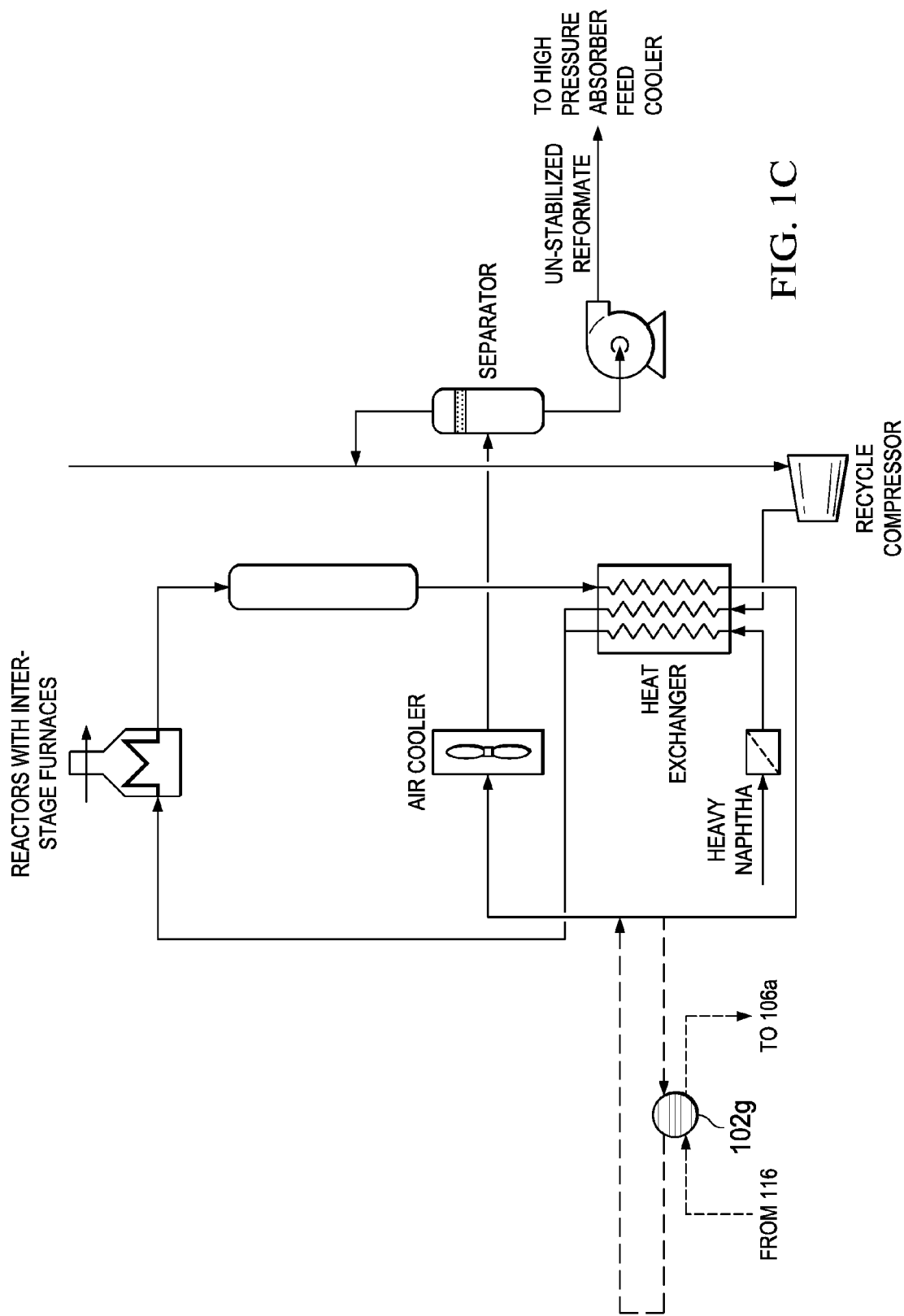
Figure 1D:
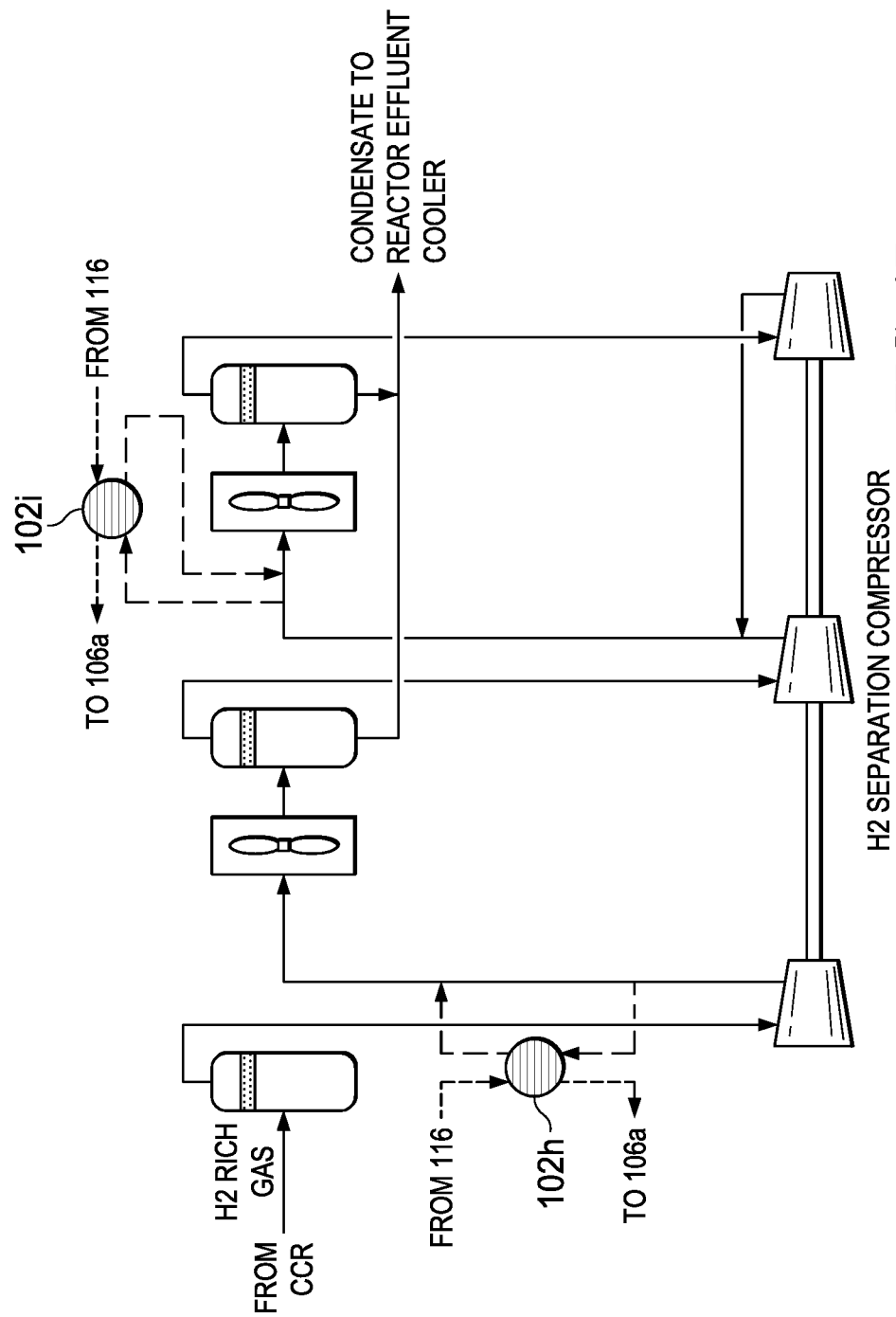
Figure 1E:
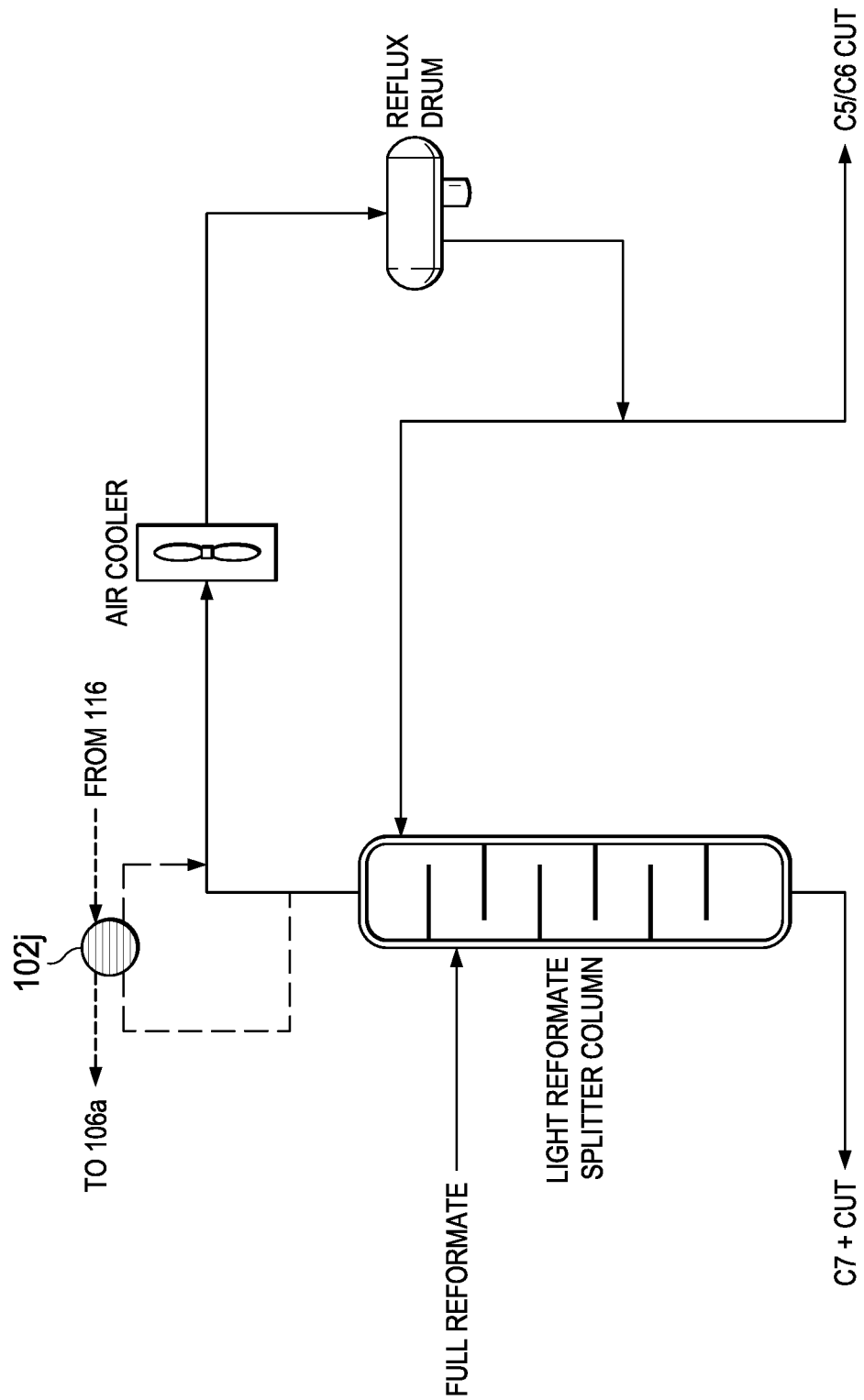
Figure 1F:
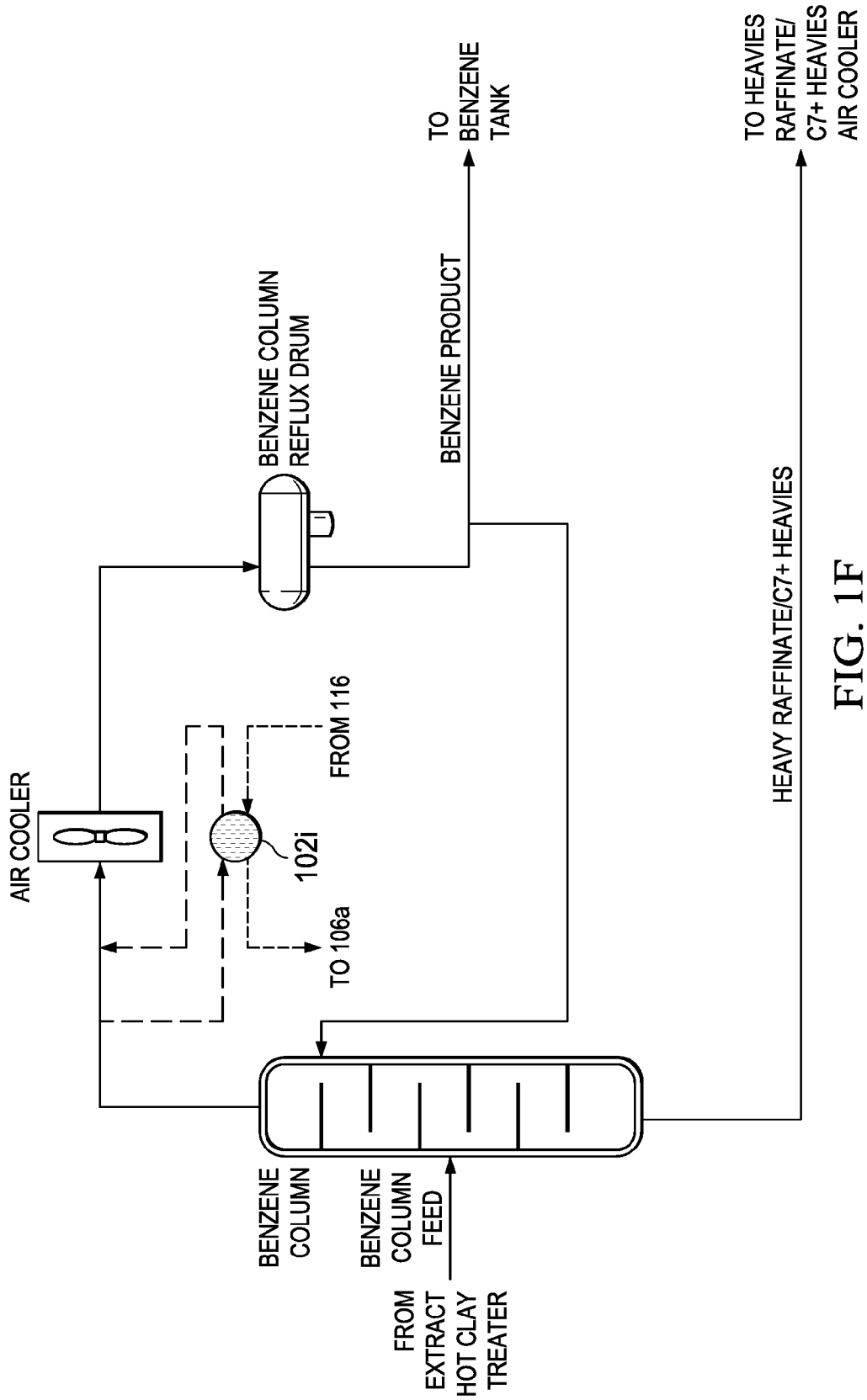
Figure 1G:
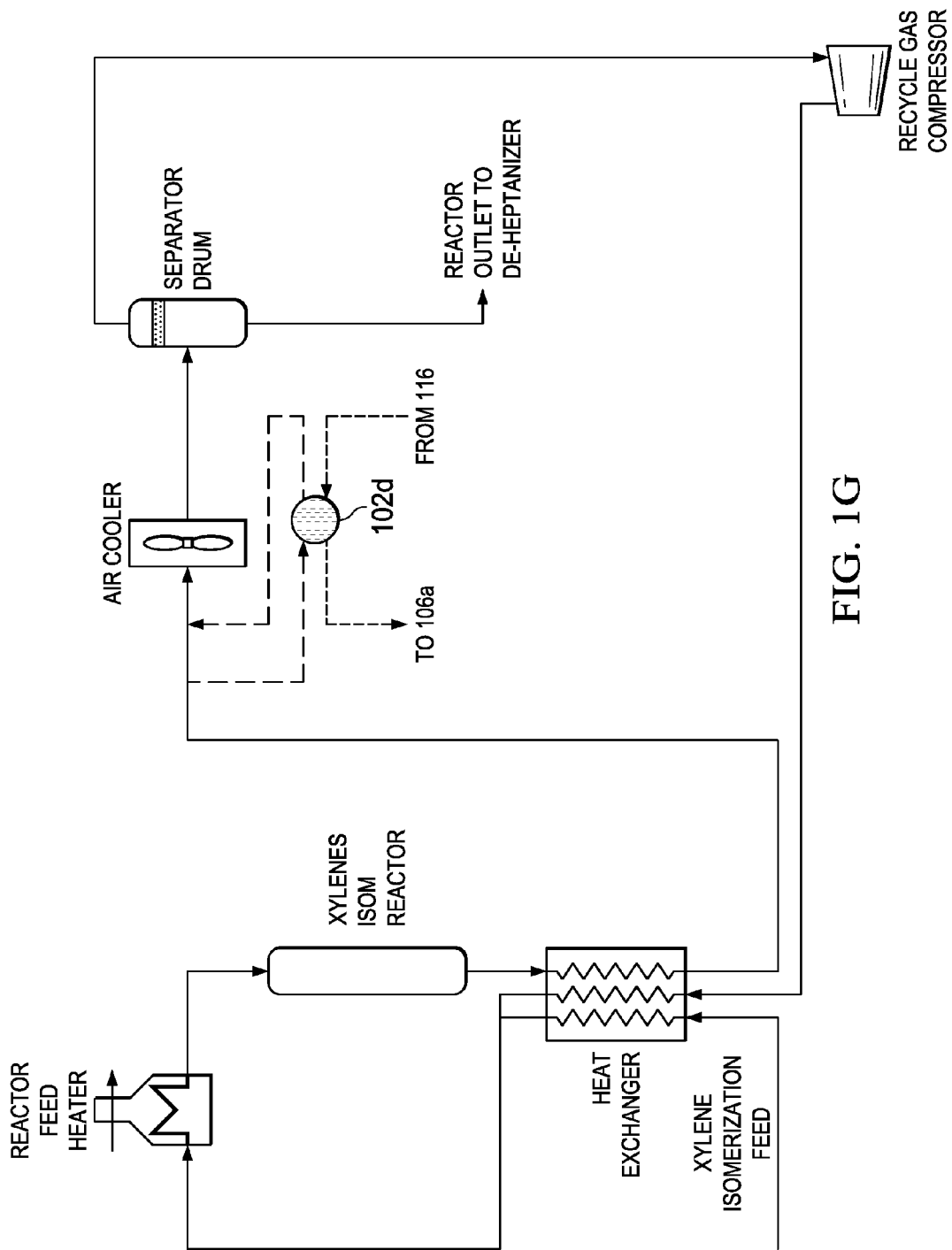
Figure 1H:
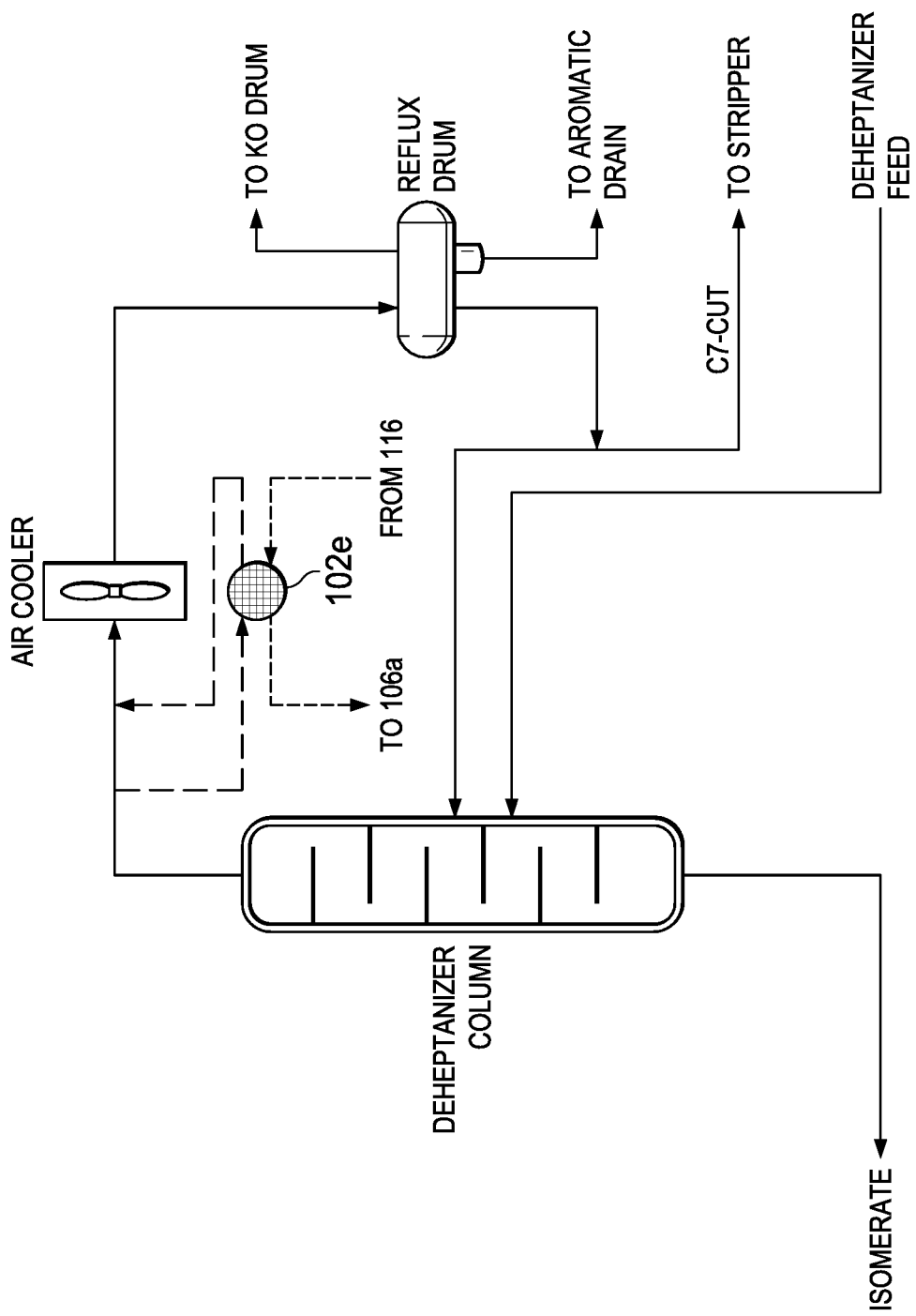
Figure 1I:
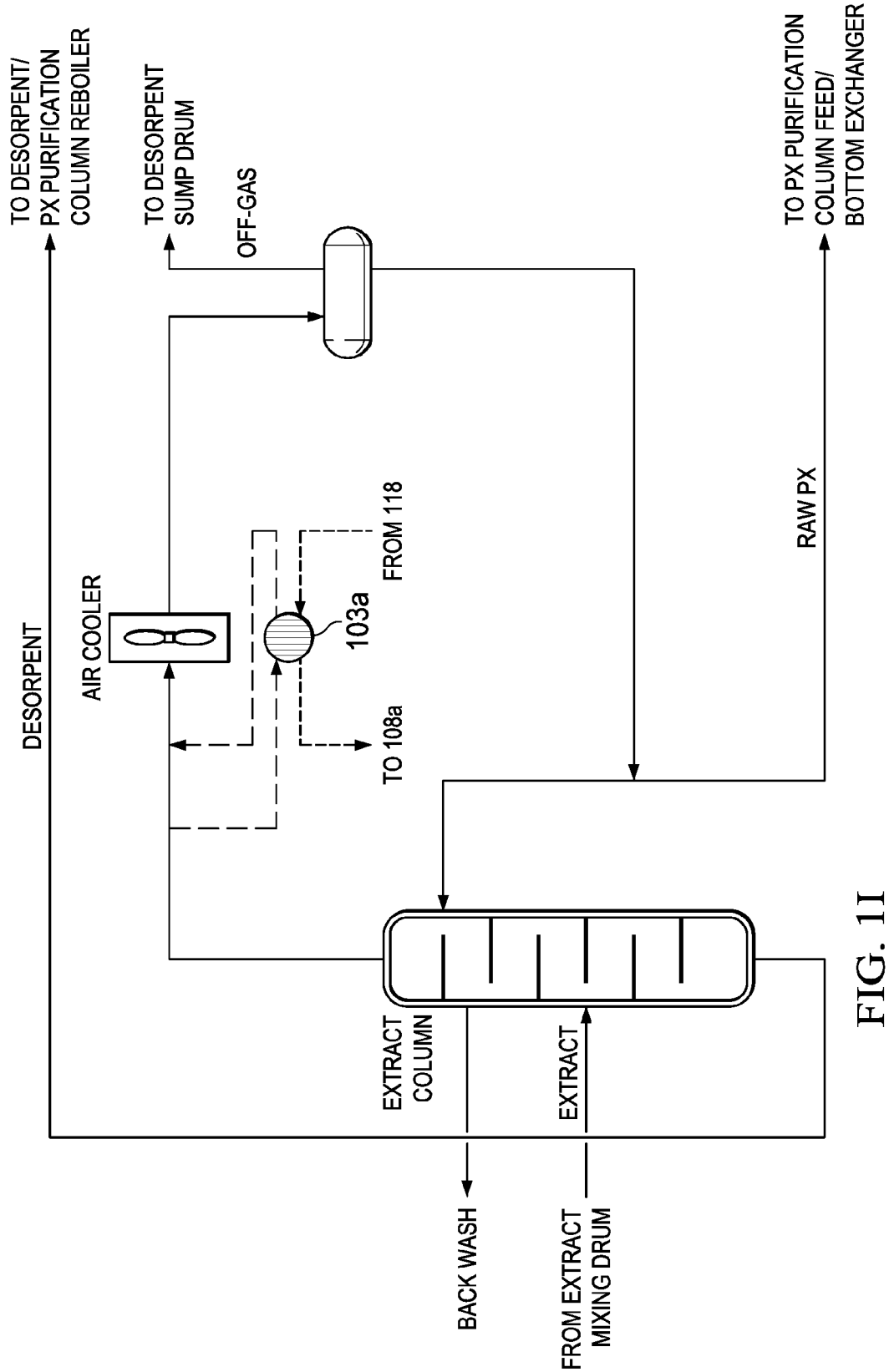
Figure 1J:
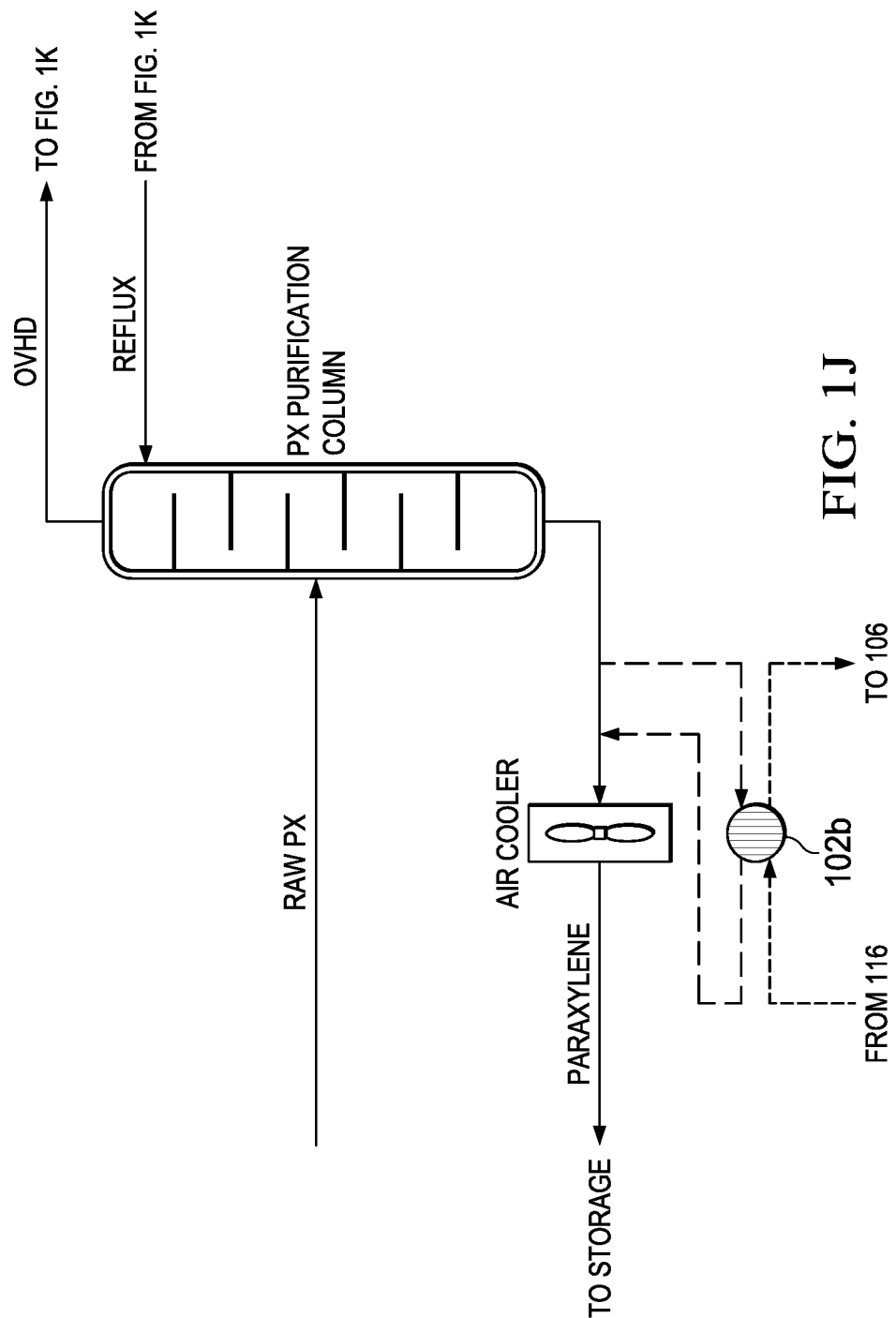
Figure 1L:
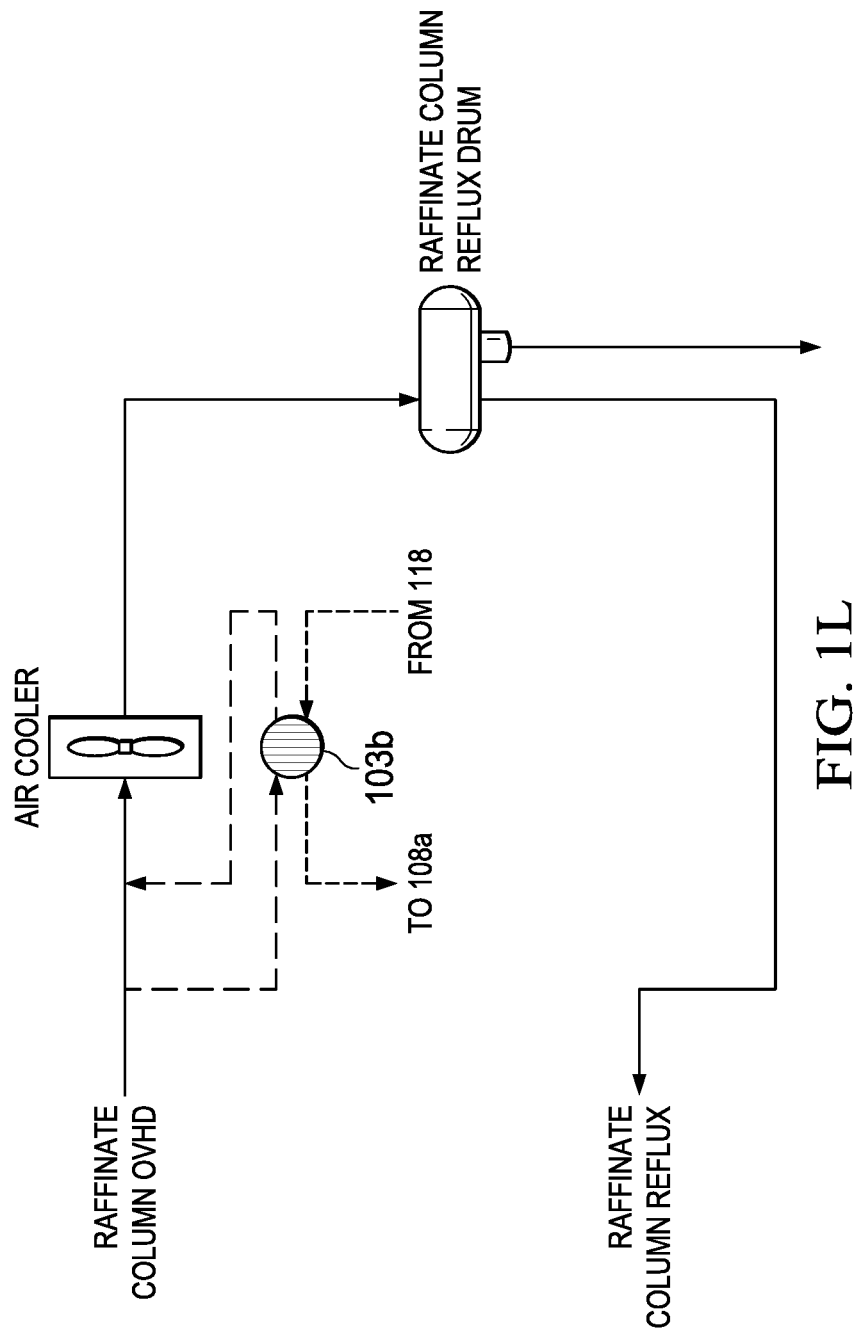
Figure 1M:
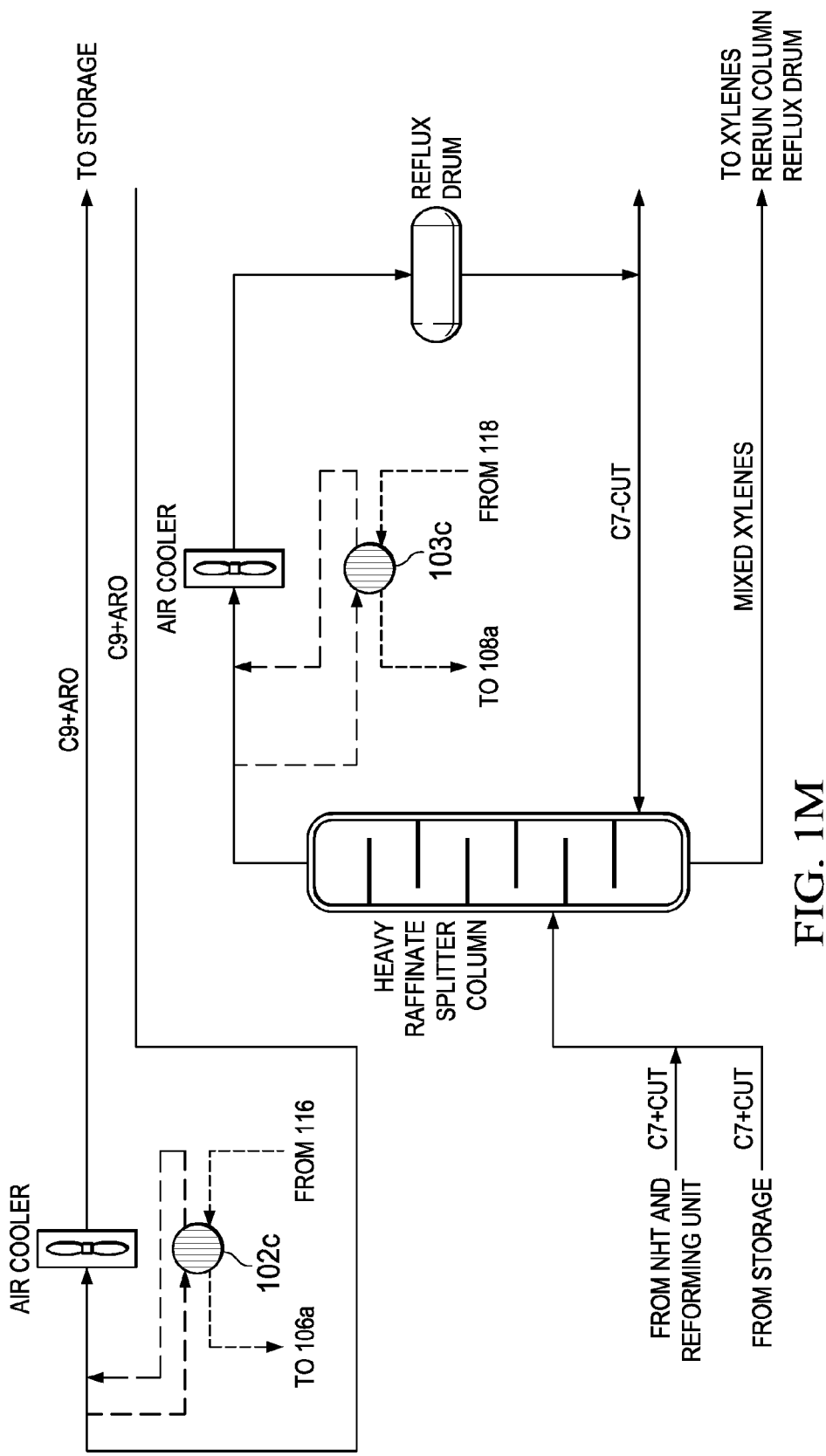
Figure 1N:
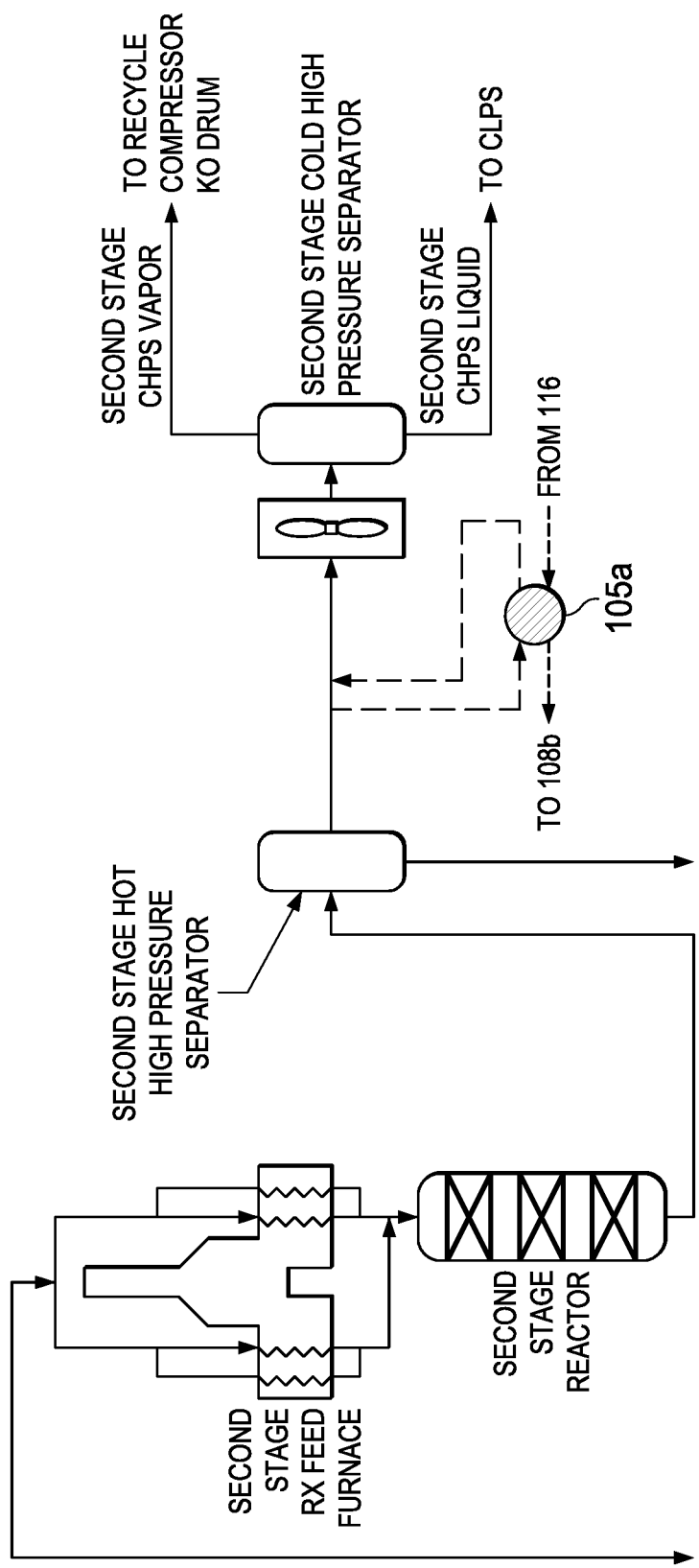
Figure 1O:
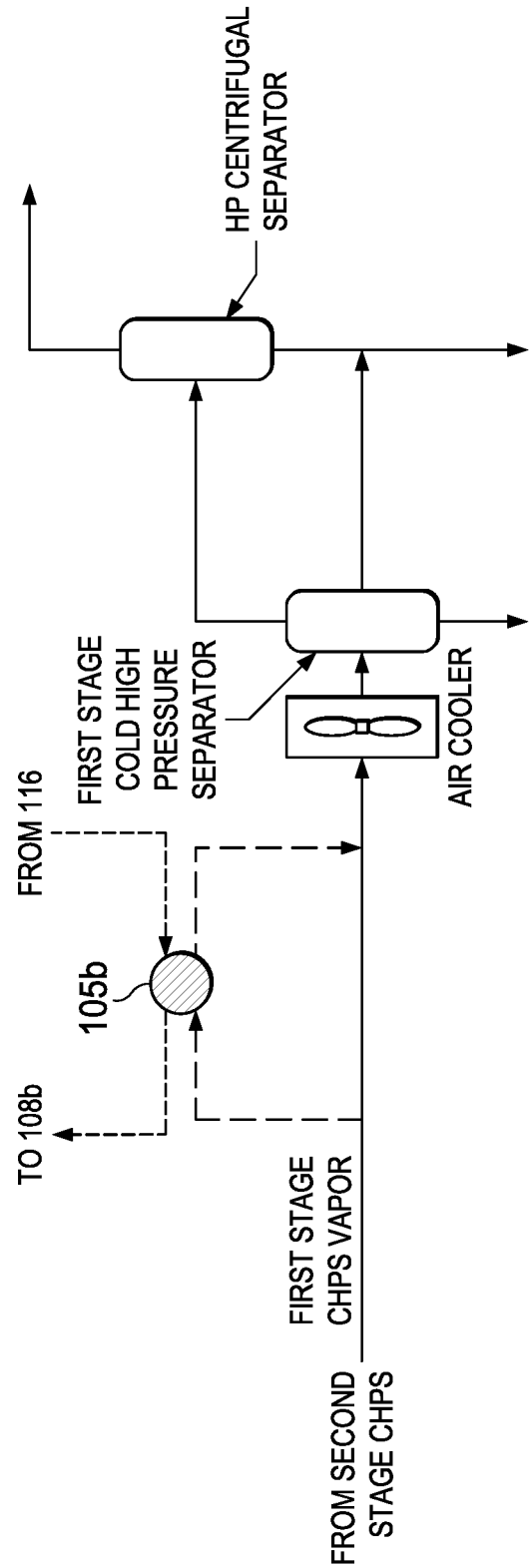
Figure 1P:
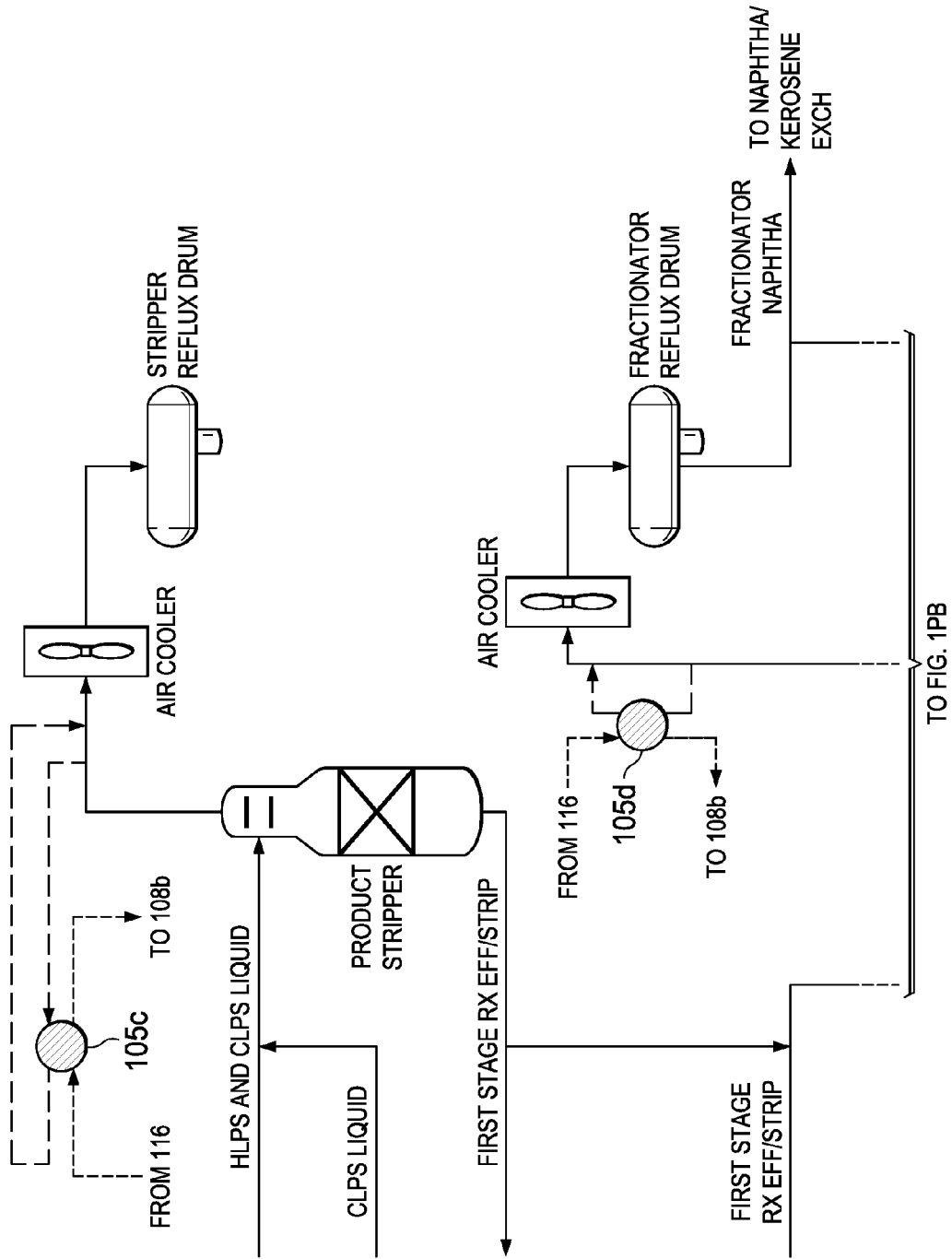
Figure 1P:
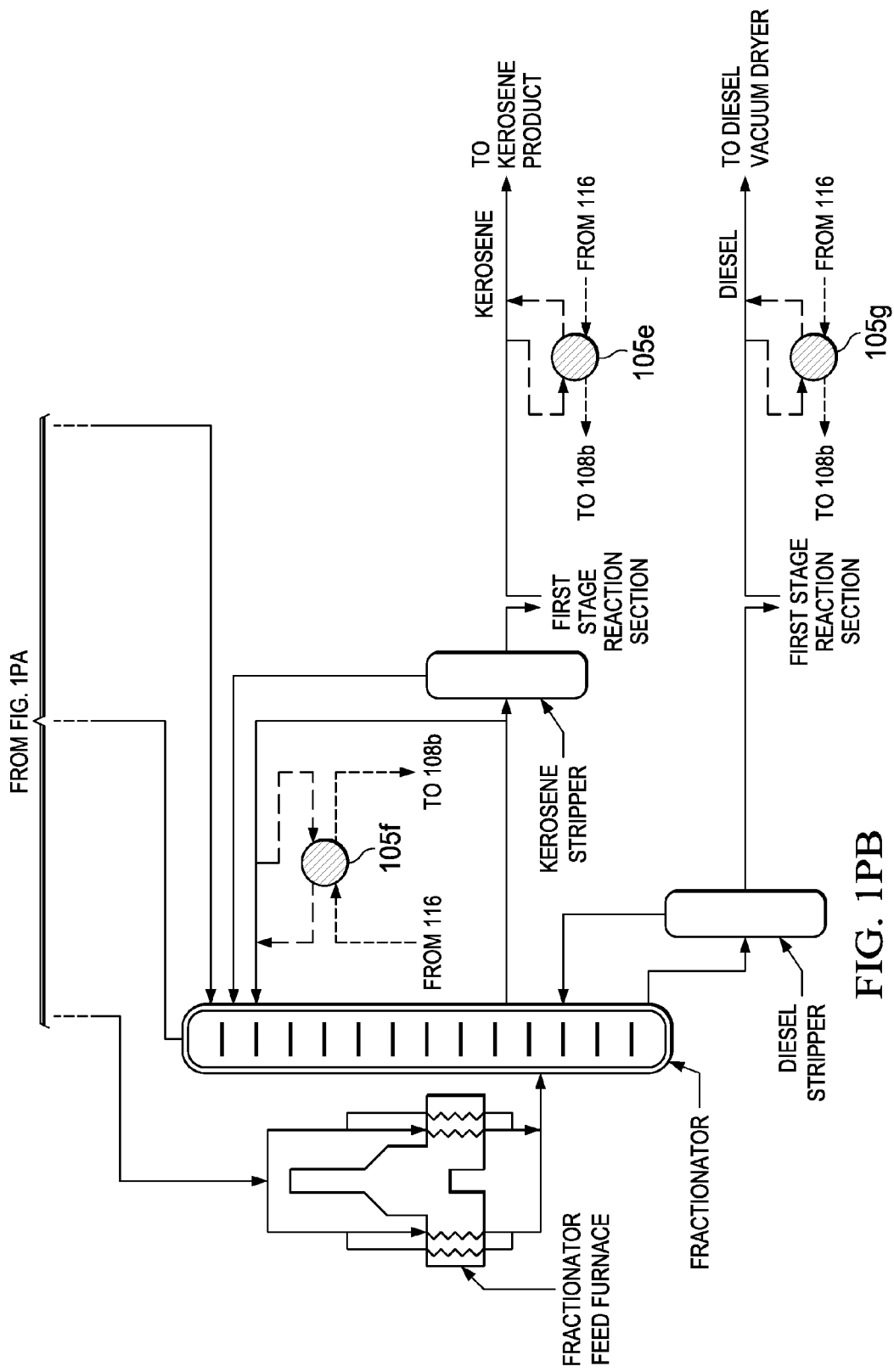
Figure 1Q:
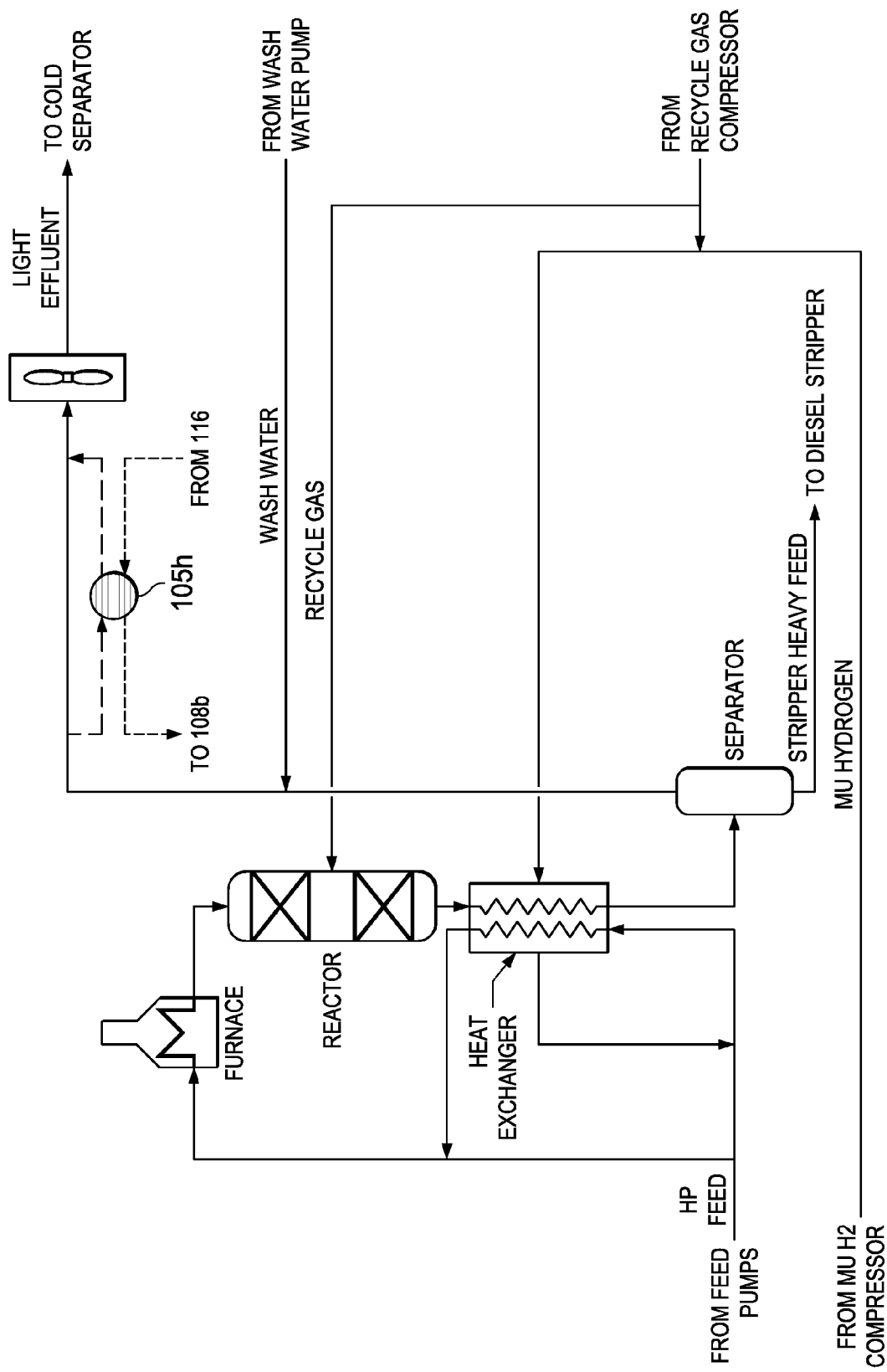
Figure 1R:
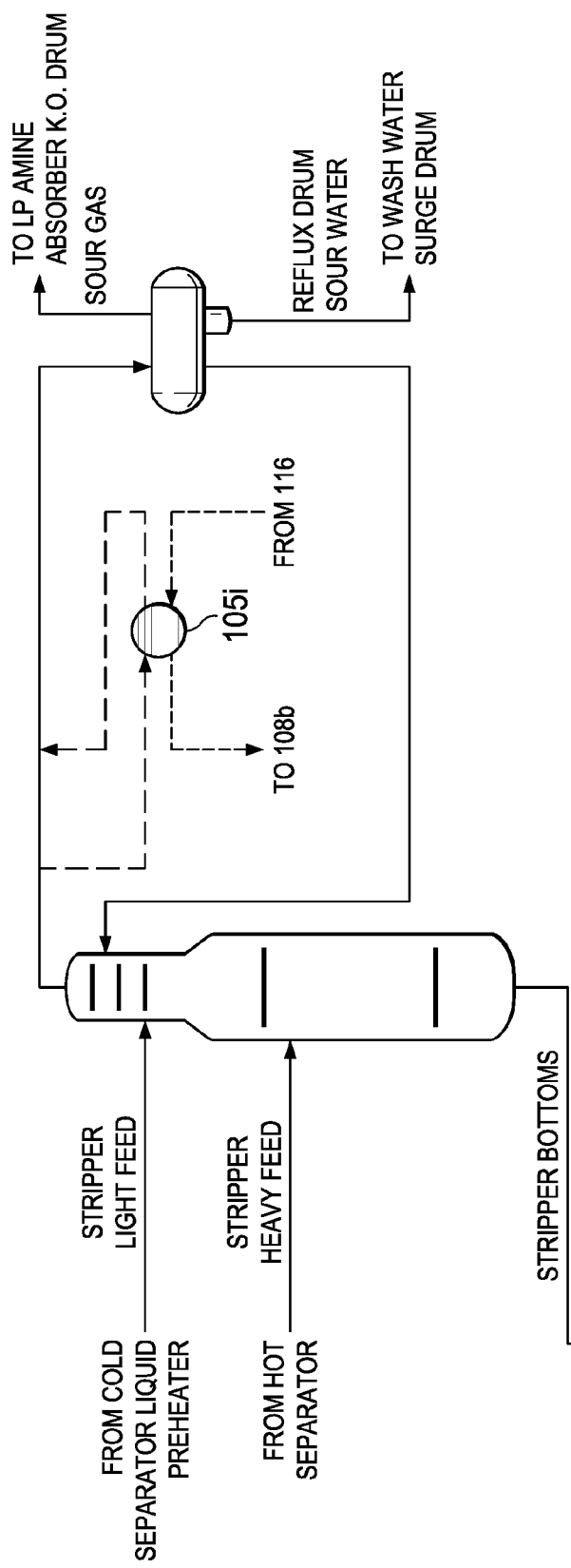
Figure 1R:
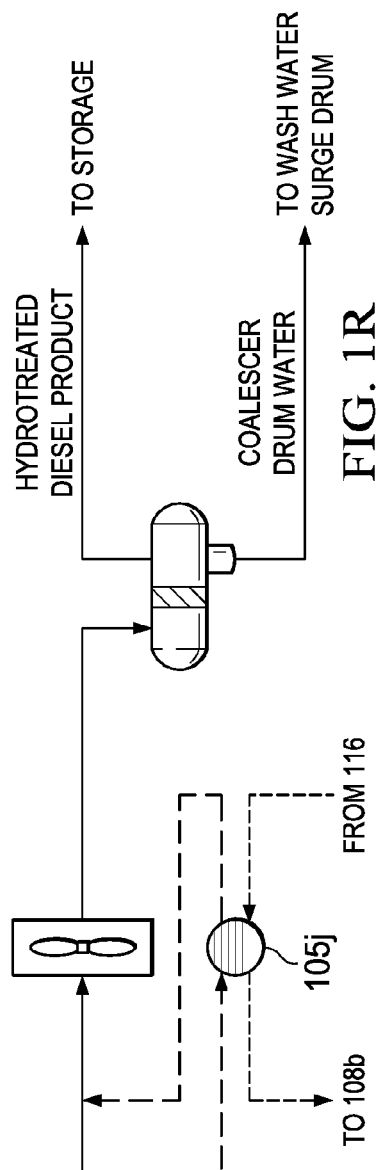
Figure 1S:
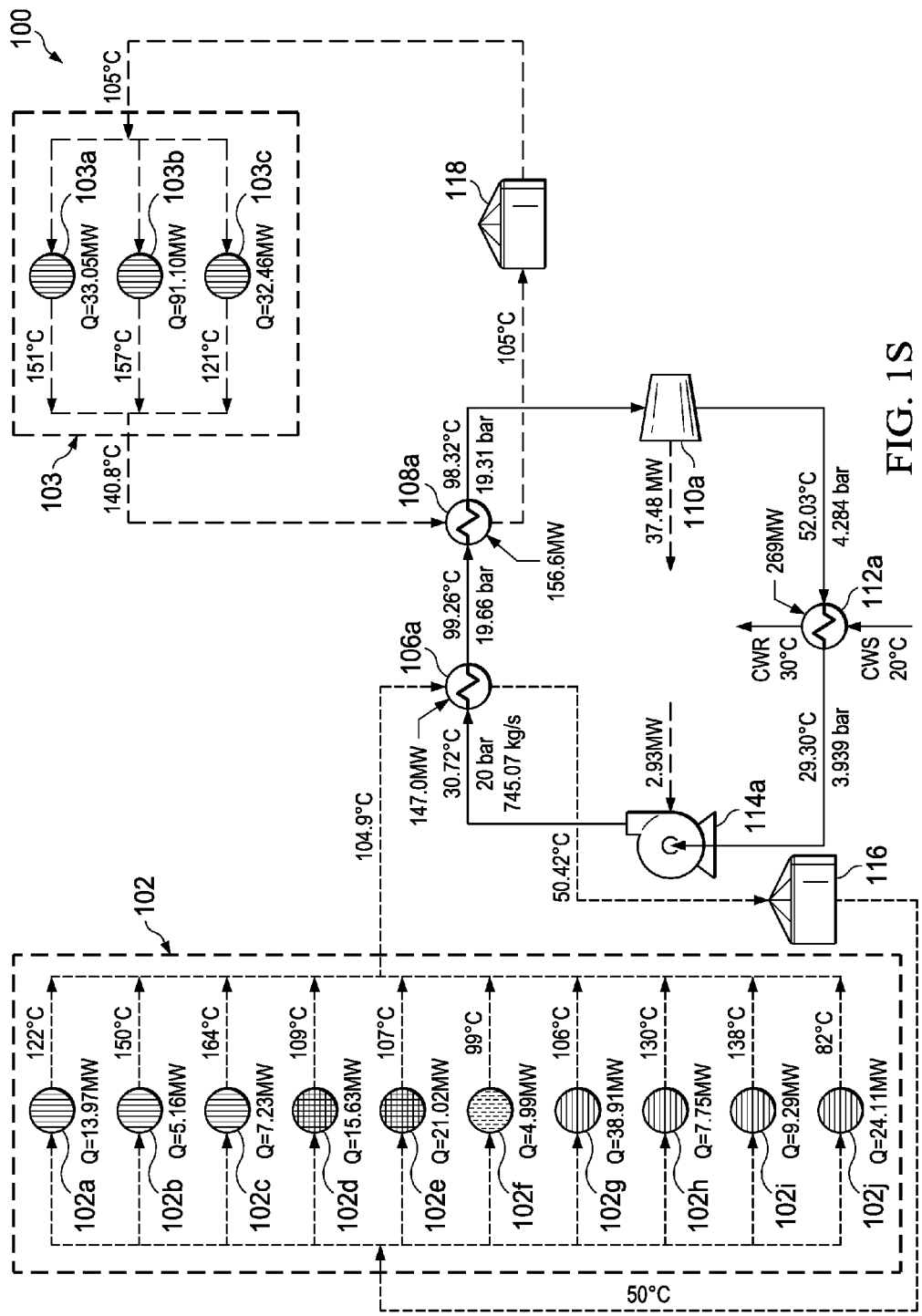
Figure 1T:
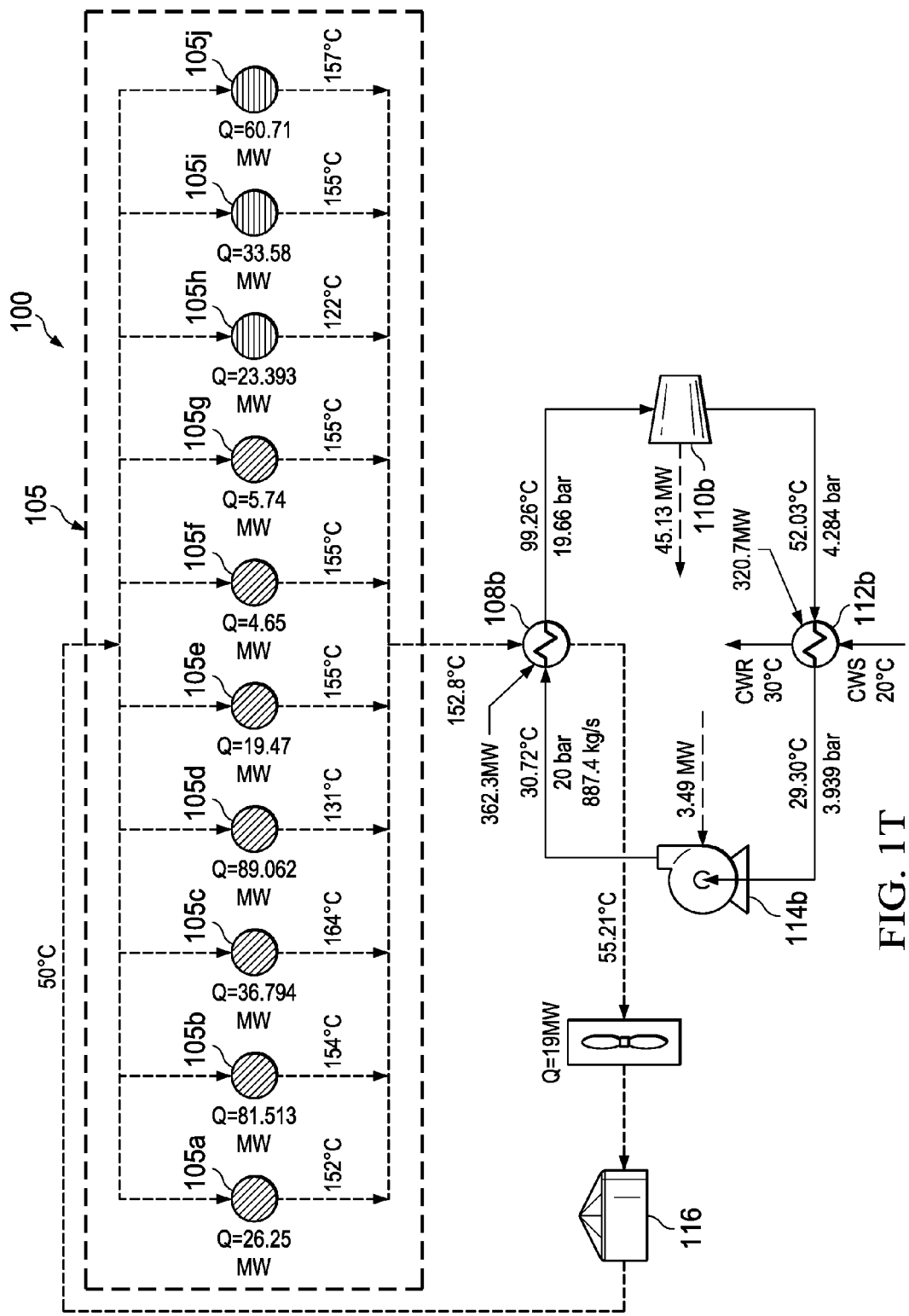
Figure 1V:
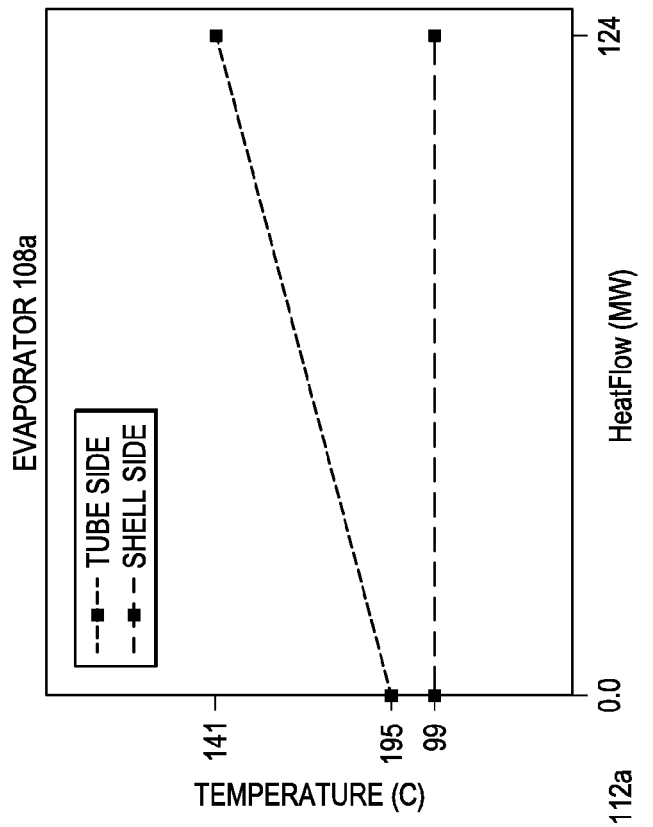
Figure 1U:
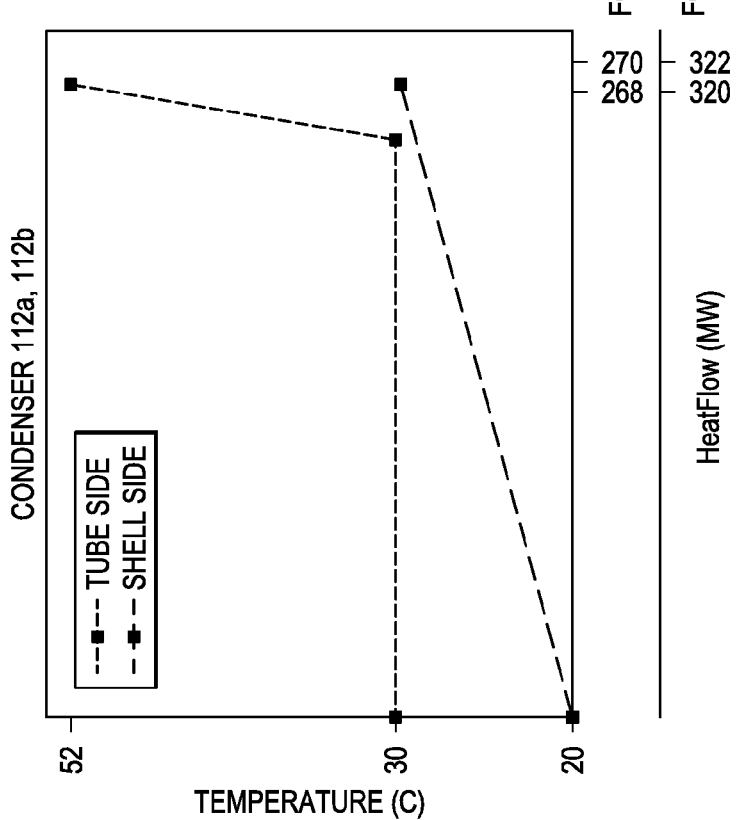

FIGS. 1A-1U illustrate schematic views of an example system 100 for a power conversion network that includes waste heat sources associated with a diesel hydrotreating-hydrocracking plant and a continuous-catalytic-cracking-aromatics plant. In this example system 100, a mini-power plant synthesis uses two independent circuits of ORC systems, sharing hot water (or other heating fluid) and isobutane systems infrastructure, to generate power from specific portions of a crude oil refining-petrochemical site-wide low-low grade waste heat sources, including hydrocracking, diesel hydrotreating and CCR, aromatics plants. In some aspects, the system 100 can be implemented in one or more steps, where each phase can be separately implemented without hindering future steps to implement the system 100. In some aspects, a minimum approach temperature across a heat exchanger used to transfer heat from a heat source to a working fluid (for example, water) can be as low as 3° C. or may be higher. Higher minimum approach temperatures can be used in the beginning of the phases at the expense of less waste heat recovery and power generation, while reasonable power generation economics of scale designs are still attractive in the level of tens of megawatts of power generation.

In some aspects of system 100, optimized efficiency is realized upon using a minimum approach temperature recommended for the specific heat source streams used in the system design. In such example situations, optimized power generation can be realized without re-changing the initial topology or the sub-set of low grade waste heat streams selected/utilized from the whole crude oil refining-petrochemical complex utilized in an initial phase. System 100 and its related process scheme can be implemented for safety and operability through two ORC systems using one or more buffer streams such as hot oil or high pressure hot water systems or a mix of specified connections among buffer systems. The low-low grade waste-heat-to-power-conversion (for example, lower than the low grade waste heat temperature defined by U.S. Department of Energy DOE as 232° C.) may be implemented using one or more ORC systems using isobutane as an organic fluid at specific operating conditions using two buffer systems shared by the two systems of power generation but can be working independently too. In some aspects of system 100, one of the two ORC systems has only an evaporator while the other ORC system has an evaporator and pre-heater.

System 100 may not change with future changes inside individual hydrocracking, hydrotreating, CCR, and aromatics plants to enhance energy efficiency and system 100 may not need to be changed upon improvements in plant waste heat recovery practices, such as heat integration among hot and cold streams. System 100 may use "low-low" grade waste heat, below 160° C. available in heat sources in the medium level crude oil semi-conversion refining facilities and aromatics complex.

FIGS. 1A-1B is a schematic diagram of an example system 100 for a power conversion network that includes waste heat sources associated with a diesel hydrotreating-hydrocracking plant and a continuous-catalytic-cracking-aromatics plant. In this example implementation, system 100 utilizes twenty-three distinct heat sources that feed heat through a working fluid (for example, hot water, hot oil, or otherwise) to two ORC systems to produce power. In the illustrated example, the twenty-three heat sources are separated among three heat recovery circuits. For instance, heat recovery circuit 102 includes heat exchangers 102a-102j. Heat recovery circuit 103 includes heat exchangers 103a-103c. Heat recovery circuit 105 includes heat exchangers 105a-105j.

In the illustrated example, each heat exchanger facilitates heat recovery from a heat source in a particular industrial unit to the working fluid. For example, heat exchangers 102a-102c recover heat from heat sources in a para-xylene separation unit. Heat exchangers 102d-102e recover heat from heat sources in a para-xylene isomerization reaction and separation unit(s). Heat exchanger 102f recovers heat from a heat source(s) in a benzene extraction unit. Heat exchangers 102g-102j recover heat from heat sources in a continuous catalytic reforming plant (CCR). Together, heat exchangers in the heat recovery circuit 102 recover low grade waste heat from specific streams in a "Naphtha Block" to deliver the heat via the working fluid to an ORC 104a. In this example, the heat from heat recovery circuit 102 is provided to a pre-heater 106a of the ORC 104a.

Generally, the heat recovery circuit 102 receives (for example, from an inlet header that fluidly couples a heating fluid tank 116 to the heat exchangers 102a-102j) high pressure working fluid (for example, hot water, hot oil, or otherwise) for instance, at between about 40° C. to 60° C. and supplies heated fluid (for example, at an outlet header fluidly coupled to the heat exchangers 102a-102j) at or about 100-115° C. The heat exchangers 102a-102j may be positioned or distributed along the CCR-Aromatics module complex and fluidly coupled to low grade waste heat sources from the refining-petrochemical plants. Para-Xylene products separation plant streams may be used as heat sources in the heat recovery circuit 102, along with other plants such as the benzene extraction unit, CCR, and xylene isomerization reaction and separation sections.

Heat exchangers 103a-103c recover heat from heat sources in a refining-petrochemicals complex portion that contains the para-xylene separation unit. Together, the heat exchangers in the heat recovery circuit 103 recover low grade waste heat to deliver the heat via the working fluid to the ORC 104a. In this example, the heat from heat recovery circuit 103 is provided to an evaporator 108a of the ORC 104a.

Generally, the heat recovery circuit 103 receives (for example, from an inlet header that fluidly couples a heating fluid tank 118 to the heat exchangers 103a-103c) high pressure working fluid (for example, hot water, hot oil, or otherwise) at or about 100-110° C. and it heats it up to about 125-160° C. The heat exchangers 103a-103c may be distributed along the CCR-Aromatics module of the refining-petrochemical complex using low grade waste heat sources in the refining-petrochemical complex plants using only para-xylene products separation plant streams.

Heat exchangers 105a-105g in heat recovery circuit 105, in this example, recover heat from heat sources in a hydrocracking plant separation unit. Heat exchangers 105h-105j in heat recovery circuit 105, in this example, recover heat from heat sources in a hydrotreating plant separation unit. Together, the heat exchangers in the heat recovery circuit 105 recover low grade waste heat to deliver the heat via the working fluid to an ORC 104b. In this example, the heat from heat recovery circuit 105 is provided to an evaporator 108b of the ORC 104b.

Generally, the heat recovery circuit 105 receives (for example, from an inlet header that fluidly couples the heating fluid tank 116 to the heat exchangers 105a-105j) high pressure working fluid (for example, hot water, hot oil, or otherwise) at or about 40-60° C. and it heats it up to about 120-160° C.

In the example implementation of system 100, the ORC 104a includes a working fluid that is thermally coupled to the heat recovery circuits 102 and 103 to heat the working fluid. In some implementations, the working fluid can be isobutane. The ORC 104a can also include a gas expander 110a (for example, a turbine-generator) configured to generate electrical power from the heated working fluid. As shown in FIG. 1A, the ORC 104a can additionally include a pre-heater 106a, an evaporator 108a, a pump 114a, and a condenser 112a. In this example implementation, the heat recovery circuit 102 supplies a heated working, or heating, fluid to the pre-heater 106a, while the heat recovery circuit 103 supplies a heated working, or heating, fluid to the evaporator 108a.

In the example implementation of system 100, the ORC 104b includes a working fluid that is thermally coupled to the heat recovery circuit 105 to heat the working fluid. In some implementations, the working fluid can be isobutane. The ORC 104b can also include a gas expander 110b (for example, a turbine-generator) configured to generate electrical power from the heated working fluid. As shown in FIG. 1B, the ORC 104b can additionally include an evaporator 108b, a pump 114b, and a condenser 114b. In this example implementation, the heat recovery circuit 105 supplies a heated working, or heating, fluid to the evaporator 108b.

In a general operation, a working, or heating, fluid (for example, water, oil, or other fluid) is circulated through the heat exchangers of the heat recovery circuits 102, 103, and 105. An inlet temperature of the heating fluid that is circulated into the inlets of each of the heat exchangers may be the same or substantially the same subject to any temperature variations that may result as the heating fluid flows through respective inlets, and may be circulated directly from a heating fluid tank 116 or 118. Each heat exchanger heats the heating fluid to a respective temperature that is greater than the inlet temperature. The heated heating fluids from the heat exchangers are combined in their respective heat recovery circuits and circulated through one of the pre-heater 106a, the evaporator 108a, or the evaporator 108b of the ORC. Heat from the heated heating fluid heats the working fluid of the respective ORC thereby increasing the working fluid pressure and temperature. The heat exchange with the working fluid results in a decrease in the temperature of the heating fluid. The heating fluid is then collected in the heating fluid tank 116 or the heating fluid tank 118 and can be pumped back through the respective heat exchangers to restart the waste heat recovery cycle.

The heating fluid circuit to flow heating fluid through the heat exchangers of system 100 can include multiple valves that can be operated manually or automatically. For example, a modulating control valve (as one example) may be positioned in fluid communication with an inlet or outlet of each heat exchanger, on the working fluid and heat source side. In some aspects, the modulating control valve may be a shut-off valve or additional shut-off valves may also be positioned in fluid communication with the heat exchangers. An operator can manually open each valve in the circuit to cause the heating fluid to flow through the circuit. To cease waste heat recovery, for example, to perform repair or maintenance or for other reasons, the operator can manually close each valve in the circuit. Alternatively, a control system, for example, a computer-controlled control system, can be connected to each valve in the circuit. The control system can automatically control the valves based, for example, on feedback from sensors (for example, temperature, pressure or other sensors), installed at different locations in the circuit. The control system can also be operated by an operator.

In the manner described earlier, the heating fluid can be looped through the heat exchangers to recover heat that would otherwise go to waste in the hydrocracking, hydrotreating, CCR, and aromatics plants, and to use the recovered waste heat to operate the power generation system. By doing so, an amount of energy needed to operate the power generation system can be decreased while obtaining the same or substantially similar power output from the power generation system. For example, the power output from the power generation system that implements the waste heat recovery network can be higher or lower than the power output from the power generation system that does not implement the waste heat recovery network. Where the power output is less, the difference may not be statistically significant. Consequently, a power generation efficiency of the petrochemical refining system can be increased.

FIG. 1C is a schematic diagram that illustrates an example placement of heat exchanger 102g in a crude oil refinery continuous catalytic reforming (CCR) plant. In an example implementation illustrated in FIGS. 1C and 1T, this heat exchanger 102g may cool down the CCR last stage reactor outlet after the feed-effluent heat exchanger stream from 111° C. to 60° C. using the high pressure working fluid stream of the heat recovery circuit 102 at 50° C. to raise the working fluid temperature to 106° C. The thermal duty of this heat exchanger 102g may be about 38.9 MW. The heating fluid stream at 106° C. is sent to the header of heat recovery circuit 102.

FIG. 1D is a schematic diagram that illustrates an example placement of heat exchangers 102h and 102i in the crude oil refinery continuous catalytic reforming (CCR) plant. In an example implementation illustrated in FIGS. 1D and 1S, these two heat exchangers 102h and 102i have thermal duties of 7.75 MW and 9.29 MW, respectively. Heat exchanger 102h cools down a 1st stage compressor outlet stream from 135° C. to 60° C. using the working fluid stream of heat recovery circuit 102 at 50° C. to raise its temperature to 130° C. The heating fluid stream at 130° C. is sent to the header of heat recovery circuit 102. The heat exchanger 102i cools down a 2nd stage compressor outlet stream from 143° C. to 60° C. using the working fluid stream of heat recovery circuit 102 at 50° C. to raise its temperature to 138° C. The heating fluid stream at 138° C. is sent to the header of heat recovery circuit 102.

FIG. 1G is a schematic diagram that illustrates an example placement of heat exchanger 102j in the crude oil refinery continuous catalytic reforming (CCR) plant. In an example implementation illustrated in FIGS. 1G and 1S, this heat exchanger 102j cools down the CCR light reformate splitter column overhead stream from 87° C. to 60° C. using the working fluid stream of heat recovery circuit 102 at 50° C. to raise the working fluid stream temperature to 82° C. The thermal duty of this heat exchanger 102j is about 24.1 MW. The heating fluid at 82° C. is sent to the header of heat recovery circuit 102.

FIG. 1F is a schematic diagram that illustrates an example placement of heat exchanger 102f in the benzene extraction unit. In an example implementation illustrated in FIGS. 1F and 1S, this heat exchanger 102f cools down an overhead stream from 104° C. to 100° C. using the working fluid stream of heat recovery circuit 102 at 50° C. to raise the working fluid stream temperature to 99° C. The thermal duty of this heat exchanger 102f is 4.99 MW. The heating fluid at 99° C. is sent to the header of heat recovery circuit 102.

FIG. 1G is a schematic diagram that illustrates an example placement of heat exchanger 102d in the Para-Xylene separation plant. In an example implementation illustrated in FIGS. 1G and 1S, this heat exchanger 102d cools down the Xylene isomerization reactor outlet stream before the separator drum from 114° C. to 60° C. using the working fluid stream of heat recovery circuit 102 at 50° C. to raise the working fluid stream temperature to 109° C. The thermal duty of this heat exchanger 102d is about 15.6 MW. The heating fluid at 109° C. is sent to the header of heat recovery circuit 102.

FIG. 1H is a schematic diagram that illustrates an example placement of heat exchanger 102e in the xylene isomerization de-heptanizer of the Para-Xylene separation plant. In an example implementation illustrated in FIGS. 1H and 1S, this heat exchanger 102e cools down the de-heptanizer column overhead stream from 112° C. to 60° C. using the working fluid stream of heat recovery circuit 102 at 50° C. to raise the working fluid stream temperature to 107° C. The thermal duty of this heat exchanger 102e is about 21 MW. The heating fluid at 107° C. is sent to the header of heat recovery circuit 102.

FIG. 1I is a schematic diagram that illustrates an example placement of heat exchanger 103a in the Para-Xylene separation plant. In an example implementation illustrated in FIGS. 1I and 1S, this heat exchanger 103a cools down an extract column overhead stream from 156° C. to 133° C. using the working fluid stream of heat recovery circuit 103 at 105° C. to raise the working fluid stream temperature to 151° C. The thermal duty of this heat exchanger 103a is about 33 MW. The heating fluid at 151° C. is sent to the header of heat recovery circuit 103.

FIG. 1J is a schematic diagram that illustrates an example placement of heat exchanger 102b in the Para-Xylene separation plant. In an example implementation illustrated in FIGS. 1J and 1S, this heat exchanger 102b cools down the PX purification column bottom product stream from 155° C. to 60° C. using the working fluid stream of heat recovery circuit 102 at 50° C. to raise the working fluid stream temperature to 150° C. The thermal duty of this heat exchanger 102b is about 5.16 MW. The heating fluid at 150° C. is sent to the header of heat recovery circuit 102.

FIG. 1K is a schematic diagram that illustrates an example placement of heat exchanger 102a in the Para-Xylene separation plant. In an example implementation illustrated in FIGS. 1K and 1S, this heat exchanger 102a cools down the PX purification column overhead stream from 127° C. to 84° C. using the working fluid stream of heat recovery circuit 102 at 50° C. to raise the working fluid stream temperature to 122° C. The thermal duty of this heat exchanger 102a is about 13.97 MW. The heating fluid at 122° C. is sent to the header of heat recovery circuit 102.

FIG. 1L is a schematic diagram that illustrates an example placement of heat exchanger 103b in the Para-Xylene separation plant. In an example implementation illustrated in FIGS. 1L and 1S, this heat exchanger 103b cools down a Raffinate column overhead stream from 162° C. to 130° C. using the working fluid stream of heat recovery circuit 103 at 105° C. to raise the working fluid stream temperature to 157° C. The thermal duty of this heat exchanger 103b is about 91.1 MW. The heating fluid at 157° C. is sent to the header of heat recovery circuit 103.

FIG. 1M is a schematic diagram that illustrates an example placement of heat exchangers 102c and 103c in the Para-Xylene separation plant. In an example implementation illustrated in FIGS. 1M and 1S, these two heat exchangers 102c and 103c have thermal duties of 7.23 MW and 32.46 MW, respectively. Heat exchanger 102c cools down the C9+ aromatics before the storage tank from 169° C. to 60° C. using the working fluid stream of heat recovery circuit 102 at 50° C. to raise its temperature to 164° C. The heating fluid stream at 164° C. is sent to the header of heat recovery circuit 102. The heat exchanger 103c cools down the heavy Raffinate splitter column overhead stream from 126° C. to 113° C. using the working fluid stream of heat recovery circuit 103 at 105° C. to raise its temperature to 121° C. The heating fluid stream at 121° C. is sent to the header of heat recovery circuit 103.

FIG. 1N is a schematic diagram that illustrates an example placement of heat exchanger 105a in the hydrocracking plant. In an example implementation illustrated in FIGS. 1N and 1T, this heat exchanger 105a cools down the 2nd reaction section 2nd stage cold high pressure separator feed stream from 157° C. to 60° C. using the working fluid stream of heat recovery circuit 105 at 50° C. to raise the working fluid stream temperature to 152° C. The thermal duty of this heat exchanger 105a is about 26.25 MW. The heating fluid at 152° C. is sent to the header of heat recovery circuit 105.

FIG. 1O is a schematic diagram that illustrates an example placement of heat exchanger 105b in the hydrocracking plant. In an example implementation illustrated in FIGS. 1O and 1T, this heat exchanger 105b cools down the 1st reaction section 1st stage cold high pressure separator feed stream from 159° C. to 60° C. using the working fluid stream of heat recovery circuit 105 at 50° C. to raise the working fluid stream temperature to 152° C. The thermal duty of this heat exchanger 105b is about 81.51 MW. The heating fluid at 152° C. is sent to the header of heat recovery circuit 105.

FIGS. 1PA and 1PB illustrates a schematic diagram that illustrates an example placement of heat exchangers 105c-105g in the hydrocracking plant. In an example implementation illustrated in FIGS. 1PA-1PB and 1S, these heat exchangers 105c-105g have thermal duties of 36.8 MW, 89 MW, 19.5 MW, 4.65 MW, and 5.74 MW, respectively. Heat exchanger 105c cools down the product stripper overhead stream from 169° C. to 60° C. using the working fluid stream of heat recovery circuit 105 at 50° C. to raise its temperature to 164° C. The heating fluid stream at 164° C. is sent to the header of heat recovery circuit 105. The heat exchanger 105d cools down the main fractionator overhead stream from 136° C. to 60° C. using the working fluid stream of heat recovery circuit 105 at 50° C. to raise its temperature to 131° C. The heating fluid stream at 131° C. is sent to the header of heat recovery circuit 105. The heat exchanger 105e cools down the kerosene product stream from 160° C. to 60° C. using the working fluid stream of heat recovery circuit 105 at 50° C. to raise its temperature to 155° C. The heating fluid stream at 155° C. is sent to the header of heat recovery circuit 105. In an example aspect, a steam generator with a thermal duty of about 5.45 MW using a hot stream temperature of 187° C. is used before this heat exchanger 105e to generate low pressure steam for process use. The heat exchanger 105f cools down the kerosene pumparound stream from 160° C. to 60° C. using the working fluid stream of heat recovery circuit 105 at 50° C. to raise its temperature to 155° C. The heating fluid stream at 155° C. is sent to the header of heat recovery circuit 105. In an example aspect, a steam generator with a thermal duty of about 5.58 MW using a hot stream temperature of 196° C. is used before this heat exchanger 105f to generate low pressure steam for process use. The heat exchanger 105g cools down the diesel product stream from 160° C. to 60° C. using the working fluid stream of heat recovery circuit 105 at 50° C. to raise its temperature to 155° C. The heating fluid stream at 155° C. is sent to the header of heat recovery circuit 105. In an example aspect, a steam generator with a thermal duty of about 6.47 MW using a hot stream temperature of 204° C. is used before this heat exchanger 105g to generate low pressure steam for process use.

FIG. 1Q is a schematic diagram that illustrates an example placement of heat exchanger 105h in the hydrotreating plant. In an example implementation illustrated in FIGS. 1Q and 1T, this heat exchanger 105h cools down the light effluent to cold separator stream from 127° C. to 60° C. using the working fluid stream of heat recovery circuit 105 at 50° C. to raise the working fluid stream temperature to 122° C. The thermal duty of this heat exchanger 105h is about 23.4 MW. The heating fluid at 122° C. is sent to the header of heat recovery circuit 105.

FIG. 1R is a schematic diagram that illustrates an example placement of heat exchangers 105i and 105j in the hydrotreating plant. In an example implementation illustrated in FIGS. 1R and 1T, these heat exchangers have thermal duties of 33.58 MW and 60.71 MW, respectively. The heat exchanger 105i cools down the diesel stripper overhead stream from 160° C. to 60° C. using the working fluid stream of heat recovery circuit 105 at 50° C. to raise the working fluid stream temperature to 155° C. The heating fluid at 155° C. is sent to the header of heat recovery circuit 105. In an example aspect, a steam generator with a thermal duty of about 6.38 MW using an overhead hot stream temperature of 182° C. is used before this heat exchanger 105i to generate low pressure steam for process use. The heat exchanger 105i cools down the diesel stripper product stream from 162° C. to 60° C. using the working fluid stream of heat recovery circuit 105 at 50° C. to raise the working fluid stream temperature to 157° C. The heating fluid at 157° C. is sent to the header of heat recovery circuit 105.

As described earlier, FIGS. 1S-1T illustrate a specific example of the system 100, including some example temperatures, thermal duties, efficiencies, power inputs, and power outputs. For example, as illustrated in FIG. 1S, the CCR-Aromatics module generates a power output (with a gas turbine 110a using efficiency of 85%) of about 37.5 MW and the power consumed in the pump using efficiency of 75% is about 2.9 MW. The ORC 104a high pressure at the inlet of the turbine is about 20 bar and at the outlet is about 4.3 bar. The condenser 112a water supply temperature is assumed to be at 20° C. and return temperature is assumed to be at 30° C. The evaporator 108a thermal duty is about 157 MW to vaporize about 745 Kg/s of isobutane. The ORC 104a isobutane pre-heater 106a thermal duty is about 147 MW to heat up the isobutane from about 31° C. to 99° C. The condenser 112a cooling duty is 269 MW to cool down and condense the same flow of isobutane from about 52° C. to 30° C.

As illustrated in FIG. 1T, the Hydrocracking-Diesel Hydrotreating module generates about 45 MW (with the gas turbine 110b using efficiency of 85%), and the power consumed in the pump 114b using efficiency of 75% is about 3.5 MW. The ORC 104b high pressure at the inlet of the turbine 110b is about 20 bar and at the outlet is about 4.3 bar. The condenser 112b water supply temperature is assumed to be at 20° C. and return temperature is assumed to be at 30° C. The evaporator 108b thermal duty is about 363 MW to pre-heat and vaporize about 887 Kg/s of isobutane from about 31° C. to 99° C., and the condenser 112b cooling duty is about 321 MW to cool down and condense the same flow of isobutane from about 52° C. to 30° C.

FIG. 1U is a graph that shows a tube side fluid temperature (for example, a cooling, or condenser, fluid flow) and a shell side fluid temperature (for example, an ORC working fluid flow) in the condensers 112a and 112b during an operation of the system 100. This graph shows a temperature difference between the fluids on the y-axis relative to a heat flow between the fluids on the x-axis. For example, as shown in this figure, as the temperature difference between the fluids decreases, a heat flow between the fluids can increase. In some aspects, the cooling fluid medium may be at or about 20° C. or even higher. In such cases, a gas expander outlet pressure (for example, pressure of the ORC working fluid exiting the gas expander) may be high enough to allow the condensation of the ORC working fluid at the available cooling fluid temperature. As shown in FIG. 1U, the condenser water (entering the tubes of the condensers 112a and 112b) enters at about 20° C. and leaves at about 30° C. The ORC working fluid (entering the shell-side of the condensers) enters as a vapor at about 52° C., and then condenses at 30° C. and leaves the condensers as a liquid at 30° C.

FIG. 1V is a graph that shows a tube side fluid temperature (for example, a heating fluid flow) and a shell side fluid temperature (for example, an ORC working fluid flow) in the evaporator 108a during an operation of the system 100. This graph shows a temperature difference between the fluids on the y-axis relative to a heat flow between the fluids on the x-axis. For example, as shown in this figure, as the temperature difference between the fluids decreases, a heat flow between the fluids can increase. For example, as shown in FIG. 1V, as the tube-side fluid (for example, the hot oil or water in the heating fluid circuit 103) is circulated through the evaporator 108a, heat is transferred from that fluid to the shell-side fluid (for example, the ORC working fluid). Thus, the tube-side fluid enters the evaporator 108a at about 141° C. and leaves the evaporator 108a at about 105° C. The shell-side fluid enters the evaporator 108a, from the pre-heater 106a, at about 99° C. (for example, as a liquid or mixed phase fluid) and leaves the evaporator 108a also at about 99° C. (for example, as a vapor with some superheating).

Figure 1X:
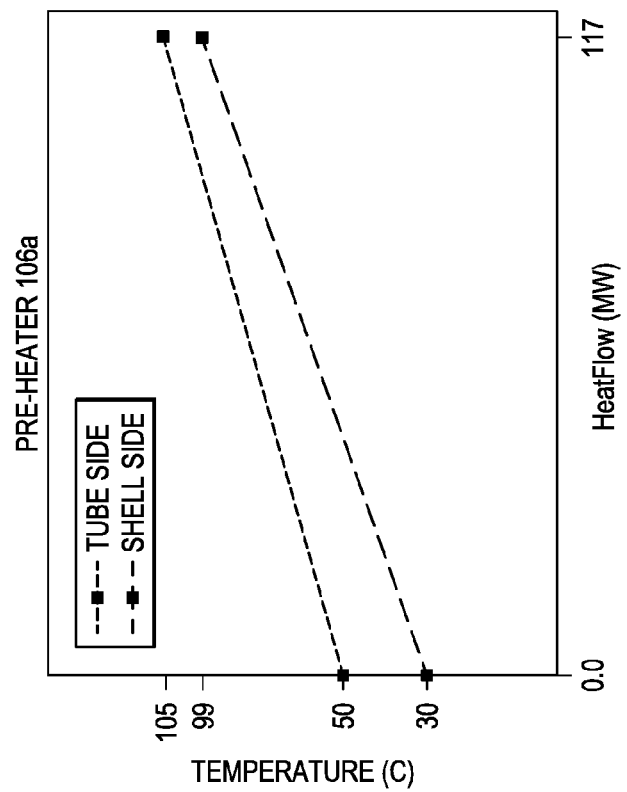
Figure 1W:
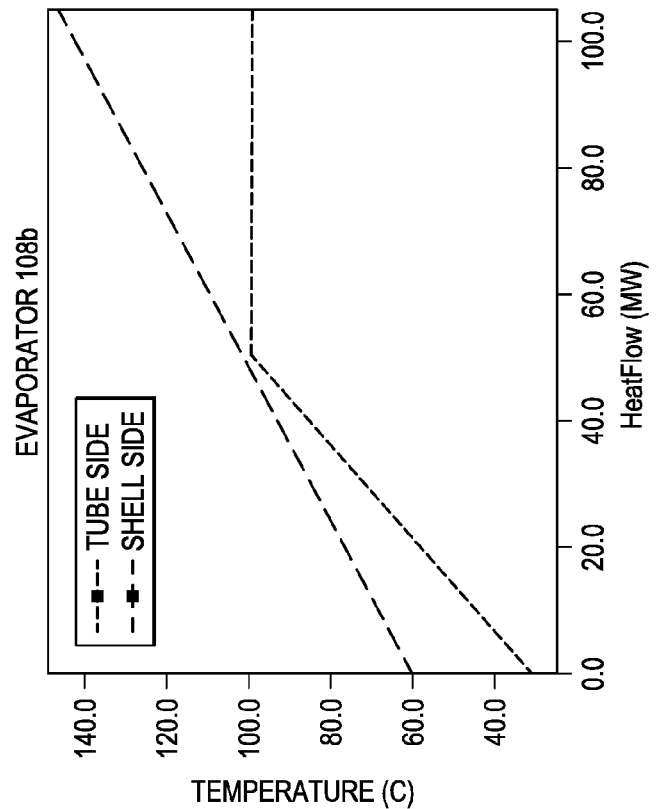

FIG. 1W is a graph that shows a tube side fluid temperature (for example, a heating fluid flow) and a shell side fluid temperature (for example, an ORC working fluid flow) in the evaporator 108b during an operation of the system 100. This graph shows a temperature difference between the fluids on the y-axis relative to a heat flow between the fluids on the x-axis. For example, as shown in this figure, as the temperature difference between the fluids decreases, a heat flow between the fluids can increase. As shown in FIG. 1W, as the tube-side fluid (for example, the hot oil or water in the heating fluid circuit 105) is circulated through the evaporator 108b, heat is transferred from that fluid to the shell-side fluid (for example, the ORC working fluid). Thus, the tube-side fluid enters the evaporator 108b at about 140° C. and leaves the evaporator 108b at about 105° C. The shell-side fluid enters the evaporator 108b at about 30° C. (for example, as a liquid) and leaves the evaporator 108b at about 99° C. (for example, as a vapor). The graph in FIG. 1W includes a "pinch point" for the shell-side fluid (for example, the ORC working fluid). The pinch point, which occurs as the fluid reaches about 99° C., represents the temperature at which the shell-side fluid vaporizes. As the shell-side fluid continues through the respective evaporator, the fluid temperature remains substantially constant (that is, about 99° C.) as the fluid complete vaporizes and, in some aspects, becomes superheated.

FIG. 1X is a graph that show a tube-side fluid temperature (for example, a heating fluid flow) and a shell-side fluid temperature (for example, an ORC working fluid flow) in the pre-heater 106a during an operation of the system 100. This graph shows a temperature difference between the fluids on the y-axis relative to a heat flow between the fluids on the x-axis. For example, as shown in this figure, as the temperature difference between the fluids decreases, a heat flow between the fluids can increase. This graph shows a temperature difference between the fluids on the y-axis relative to a heat flow between the fluids on the x-axis. For example, as shown in FIG. 1X, as the tube-side fluid (for example, the hot oil or water in the heating fluid circuit 102) is circulated through the pre-heater 106a, heat is transferred from that fluid to the shell-side fluid (for example, the ORC working fluid). Thus, the tube-side fluid enters the pre-heater 106a at about 105° C. and leaves the pre-heater 106a at about 50° C. The shell-side fluid enters the pre-heater 106a at about 30° C. (for example, as a liquid) and leaves the pre-heater 106a at about 99° C. (for example, also as a liquid or mixed phase fluid).

In the illustrated example, system 100 may include two-independent modules-based power generation using a diesel hydrotreating-hydrocracking plant module and a continuous-catalytic-cracking-aromatics plant module for a more energy efficient and "greener" configuration in refining-petrochemical complex via converting its low-low grade waste heat to net power by about 76 MW for local utilization or export to the national electricity grid. System 100 may facilitate the reduction in power-generation-based GHG emissions with desired operability due to the independent nature of the two modules in the scheme.

The techniques to recover heat energy generated by a petrochemical refining system described above can be implemented in at least one or both of two example scenarios. In the first scenario, the techniques can be implemented in a petrochemical refining system that is to be constructed. For example, a geographic layout to arrange multiple sub-units of a petrochemical refining system can be identified. The geographic layout can include multiple sub-unit locations at which respective sub-units are to be positioned. Identifying the geographic layout can include actively determining or calculating the location of each sub-unit in the petrochemical refining system based on particular technical data, for example, a flow of petrochemicals through the sub-units starting from crude petroleum and resulting in refined petroleum. Identifying the geographic layout can alternatively or in addition include selecting a layout from among multiple previously-generated geographic layouts. A first subset of sub-units of the petrochemical refining system can be identified. The first subset can include at least two (or more than two) heat-generating sub-units from which heat energy is recoverable to generate electrical power. In the geographic layout, a second subset of the multiple sub-unit locations can be identified. The second subset includes at least two sub-unit locations at which the respective sub-units in the first subset are to be positioned. A power generation system to recover heat energy from the sub-units in the first subset is identified. The power generation system can be substantially similar to the power generation system described earlier. In the geographic layout, a power generation system location can be identified to position the power generation system. At the identified power generation system location, a heat energy recovery efficiency is greater than a heat energy recovery efficiency at other locations in the geographic layout. The petrochemical refining system planners and constructors can perform modeling and/or computer-based simulation experiments to identify an optimal location for the power generation system to maximize heat energy recovery efficiency, for example, by minimizing heat loss when transmitting recovered heat energy from the at least two heat-generating sub-units to the power generation system. The petrochemical refining system can be constructed according to the geographic layout by positioning the multiple sub-units at the multiple sub-unit locations, positioning the power generation system at the power generation system location, interconnecting the multiple sub-units with each other such that the interconnected multiple sub-units are configured to refine petrochemicals, and interconnecting the power generation system with the sub-units in the first subset such that the power generation system is configured to recover heat energy from the sub-units in the first subset and to provide the recovered heat energy to the power generation system. The power generation system is configured to generate power using the recovered heat energy.

In the second scenario, the techniques can be implemented in an operational petrochemical refining system. In other words, the power generation system described earlier can be retrofitted to an already constructed and operational petrochemical refining system.

In summary, this disclosure describes configurations and related processing schemes of mini-power plants synthesized for grassroots medium grade crude oil semi-conversion refineries to generate power from specific portions of low grade waste heat sources. The disclosure also describes configurations and related processing schemes of mini-power plants synthesized for integrated medium grade crude oil semi-conversion refineries and aromatics complex for power generation from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by carbon-free power generation from specific portions of low grade waste heat sources.

Thus, particular implementations of the subject matter have been described. Other implementations are within the scope of the following claims.

What is claimed is:
1. A power generation system, comprising:
a first heating fluid circuit thermally coupled to a first plurality of heat sources from a first plurality of sub-units of a petrochemical refining system, the first plurality of sub-units comprising a continuous catalytic reforming (CCR) and aromatics refining system;
a second heating fluid circuit thermally coupled to a second plurality of heat sources of a second plurality of sub-units of the petrochemical refining system, the second plurality of sub-units comprising the CCR and aromatics refining system;
a third heating fluid circuit thermally coupled to a third plurality of heat sources from a third plurality of sub-units of the petrochemical refining system, the third plurality of sub-units comprising a hydrocracking-diesel hydrotreating system;
a first power generation system that comprises a first organic Rankine cycle (ORC), the first ORC comprising (i) a first working fluid that is thermally coupled to the first and second heating fluid circuits to heat the first working fluid, and (ii) a first expander configured to generate electrical power from the heated first working fluid;
a second power generation system that comprises a second ORC, the second ORC comprising (i) a second working fluid that is thermally coupled to the third heating fluid circuit to heat the second working fluid, and (ii) a second expander configured to generate electrical power from the heated second working fluid; and
a control system configured to actuate a first set of control valves to selectively thermally couple the first heating fluid circuit to at least a portion of the first plurality of heat sources, the control system also configured to actuate a second set of control valves to selectively thermally couple the second heating fluid circuit to at least a portion of the second plurality of heat sources, the control system also configured to actuate a third set of control valves to selectively thermally couple the third heating fluid circuit to at least a portion of the third plurality of heat sources.

2. The power generation system of claim 1, wherein the first working fluid is thermally coupled to the first heating fluid circuit in a pre-heating heat exchanger of the first ORC, and the first working fluid is thermally coupled to the second heating fluid circuit in an evaporator of the first ORC.

3. The power generation system of claim 1, wherein the first heating fluid circuit comprises a first heating fluid tank that is fluidly coupled to the first and third heating fluid circuits and the pre-heating heat exchanger of the first ORC, and the second heating fluid circuit comprises a second heating fluid tank that is fluidly coupled with the evaporator of the first ORC.

4. The power generation system of claim 1, wherein the second working fluid is thermally coupled to the third heating fluid circuit in an evaporator of the second ORC.

5. The power generation system of claim 1, wherein at least one of the first or second working fluids comprises isobutane.

6. The power generation system of claim 1, wherein at least one of the first, second, or third heating fluid circuits comprises water or oil.

7. The power generation system of claim 1, wherein the first ORC further comprises:
   a condenser fluidly coupled to a condenser fluid source to cool the first working fluid and a pump to circulate the first working fluid through the first ORC, and
   the second ORC further comprises a condenser fluidly coupled to the condenser fluid source to cool the second working fluid and a pump to circulate the second working fluid through the second ORC.

8. The power generation system of claim 1, wherein
   a first sub-set of the first plurality of heat sources comprises at least three para-xylene separation unit heat sources, comprising:
      a first para-xylene separation unit heat source comprising a heat exchanger that is fluidly coupled to a raw paraxylene stream circulated through an air cooler to a storage tank, and is fluidly coupled to the first heating fluid circuit,
      a second para-xylene separation unit heat source comprising a heat exchanger that is fluidly coupled to a paraxylene purification stream circulated through an air cooler to a paraxylene purification reflux drum, and is fluidly coupled to the first heating fluid circuit, and
      a third para-xylene separation unit heat source comprising a heat exchanger that is fluidly coupled to a C9+ARO stream circulated through an air cooler to a C9+ARO storage, and is fluidly coupled to the first heating fluid circuit;
   a second sub-set of the first plurality of heat sources comprises at least two para-xylene separation-xylene isomerization reaction and separation unit heat sources, comprising:
      a first para-xylene separation-xylene isomerization reaction and separation unit heat source comprising a heat exchanger that is fluidly coupled to a Xylene isomerization reactor outlet stream before a separator drum, and is fluidly coupled to the first heating fluid circuit, and
      a second para-xylene separation-xylene isomerization reaction and separation unit heat source comprising a heat exchanger that is fluidly coupled to a de-heptanizer column overhead stream, and is fluidly coupled to the first heating fluid circuit;
   a third sub-set of the first plurality of heat sources comprises an aromatics complex-benzene extraction unit heat source comprising a heat exchanger that is fluidly coupled to an overhead stream, and is fluidly coupled to the first heating fluid circuit; and
   a fourth sub-set of the first plurality of heat sources comprises at least four continuous catalytic cracking heat sources, comprising:
      a first continuous catalytic cracking heat source comprising a heat exchanger that is fluidly coupled to a CCR last stage reactor outlet after a feed-effluent heat exchanger stream, and is fluidly coupled to the first heating fluid circuit,
      a second continuous catalytic cracking heat source comprising a heat exchanger that is fluidly coupled to a 1st stage compressor outlet stream, and is fluidly coupled to the first heating fluid circuit,
      a third continuous catalytic cracking heat source comprising a heat exchanger that is fluidly coupled to a 2nd stage compressor outlet stream, and is fluidly coupled to the first heating fluid circuit, and
      a fourth continuous catalytic cracking heat source comprising a heat exchanger that is fluidly coupled to a CCR light reformate splitter column overhead stream, and is fluidly coupled to the first heating fluid circuit.

9. The power generation system of claim 8, wherein a first sub-set of the second plurality of heat sources comprises at least three para-xylene separation unit heat sources, comprising:
   a first para-xylene separation unit heat source comprising a heat exchanger that is fluidly coupled to an extract column overhead stream, and is fluidly coupled to the second heating fluid circuit,
   a second para-xylene separation unit heat source comprising a heat exchanger that is fluidly coupled to a Raffinate column overhead stream, and is fluidly coupled to the second heating fluid circuit, and
   a third para-xylene separation unit heat source comprising a heat exchanger that is fluidly coupled to a heavy Raffinate splitter column overhead stream, and is fluidly coupled to the second heating fluid circuit.

10. The power generation system of claim 9, wherein
   a first sub-set of the third plurality of heat sources comprises at least three diesel hydrotreating reaction and stripping heat sources, comprising:
      a first diesel hydrotreating reaction and stripping heat source comprising a heat exchanger that is fluidly coupled to a light effluent to cold separator stream, and is fluidly coupled to the third heating fluid circuit,
      a second diesel hydrotreating reaction and stripping heat source comprising a heat exchanger that is fluidly coupled to a diesel stripper overhead stream, and is fluidly coupled to the third heating fluid circuit,
      a third diesel hydrotreating reaction and stripping heat source comprising a heat exchanger that is fluidly coupled to a diesel stripper product stream, and is fluidly coupled to the third heating fluid circuit; and
   a second sub-set of the third plurality of heat sources comprises at least seven hydrocracking plant heat sources, comprising:
      a first hydrocracking plant heat source comprising a heat exchanger that is fluidly coupled to a 2nd reaction section 2nd stage cold high pressure separator feed stream, and is fluidly coupled to the third heating fluid circuit,
      a second hydrocracking plant heat source comprising a heat exchanger that is fluidly coupled to a 1st reaction section 1st stage cold high pressure separator feed stream, and is fluidly coupled to the third heating fluid circuit,
      a third hydrocracking plant heat source comprising a heat exchanger that is fluidly coupled to a product stripper overhead stream, and is fluidly coupled to the third heating fluid circuit, a fourth hydrocracking plant heat source comprising a heat exchanger that is fluidly coupled to a main fractionator overhead stream, and is fluidly coupled to the third heating fluid circuit, a fifth hydrocracking plant heat source comprising a heat exchanger that is fluidly coupled to a kerosene product stream, and is fluidly coupled to the third heating fluid circuit, a sixth hydrocracking plant heat source comprising a heat exchanger that is fluidly coupled to a kerosene pumparound stream, and is fluidly coupled to the third heating fluid circuit, and a seventh hydrocracking plant heat source comprises a heat exchanger that is fluidly coupled to a diesel product stream, and is fluidly coupled to the third heating fluid circuit.

11. A method of recovering heat energy generated by a petrochemical refining system, the method comprising:

circulating a first heating fluid through a first heating fluid circuit thermally coupled to a first plurality of heat sources from a first plurality of sub-units of a petrochemical refining system, the first plurality of sub-units comprising a continuous catalytic reforming (CCR) and aromatics refining system;

circulating a second heating fluid through a second heating fluid circuit thermally coupled to a second plurality of heat sources of a second plurality of sub-units of the petrochemical refining system, the second plurality of sub-units comprising the CCR and aromatics refining system;

circulating a third heating fluid through a third heating fluid circuit thermally coupled to a third plurality of heat sources from a third plurality of sub-units of the petrochemical refining system, the third plurality of sub-units comprising a hydrocracking-diesel hydrotreating system;

generating electrical power through a first power generation system that comprises a first organic Rankine cycle (ORC), the first ORC comprising (i) a first working fluid that is thermally coupled to the first and second heating fluid circuits to heat the first working fluid with the first and second heating fluids, and (ii) a first expander configured to generate electrical power from the heated first working fluid;

generating electrical power through a second power generation system that comprises a second ORC, the second ORC comprising (i) a second working fluid that is thermally coupled to the third heating fluid circuit to heat the second working fluid with the third heating fluid, and (ii) a second expander configured to generate electrical power from the heated second working fluid;

actuating, with a control system, a first set of control valves to selectively thermally couple the first heating fluid circuit to at least a portion of the first plurality of heat sources to heat the first heating fluid with the first plurality of heat sources;

actuating, with the control system, a second set of control valves to selectively thermally couple the second heating fluid circuit to at least a portion of the second plurality of heat sources to heat the second heating fluid with the second plurality of heat sources; and actuating, with the control system, a third set of control valves to selectively thermally couple the third heating fluid circuit to at least a portion of the third plurality of heat sources to heat the third heating fluid with the third plurality of heat sources.

12. The method of claim 11, wherein the first working fluid is thermally coupled to the first heating fluid circuit in a pre-heating heat exchanger of the first ORC, and the first working fluid is thermally coupled to the second heating fluid circuit in an evaporator of the first ORC.

13. The method of claim 11, wherein the first heating fluid circuit comprises a first heating fluid tank that is fluidly coupled to the first and third heating fluid circuits and the pre-heating heat exchanger of the first ORC, and the second heating fluid circuit comprises a second heating fluid tank that is fluidly coupled with the evaporator of the first ORC.

14. The method of claim 11, wherein the second working fluid is thermally coupled to the third heating fluid circuit in an evaporator of the second ORC.

15. The method of claim 11, wherein at least one of the first or second working fluids comprises isobutane.

16. The method of claim 11, wherein at least one of the first, second, or third heating fluid circuits comprises water or oil.

17. The method of claim 11, wherein the first ORC further comprises:

a condenser fluidly coupled to a condenser fluid source to cool the first working fluid and a pump to circulate the first working fluid through the first ORC, and the second ORC further comprises a condenser fluidly coupled to the condenser fluid source to cool the second working fluid and a pump to circulate the second working fluid through the second ORC.

18. The method of claim 11, wherein a first sub-set of the first plurality of heat sources comprises at least three para-xylene separation unit heat sources, comprising:

a first para-xylene separation unit heat source comprising a heat exchanger that is fluidly coupled to a raw paraxylene stream circulated through an air cooler to a storage tank, and is fluidly coupled to the first heating fluid circuit, a second para-xylene separation unit heat source comprising a heat exchanger that is fluidly coupled to a paraxylene purification stream circulated through an air cooler to a paraxylene purification reflux drum, and is fluidly coupled to the first heating fluid circuit, and a third para-xylene separation unit heat source comprising a heat exchanger that is fluidly coupled to a C9+ARO stream circulated through an air cooler to a C9+ARO storage, and is fluidly coupled to the first heating fluid circuit;

a second sub-set of the first plurality of heat sources comprises at least two para-xylene separation-xylene isomerization reaction and separation unit heat sources, comprising:

a first para-xylene separation-xylene isomerization reaction and separation unit heat source comprising a heat exchanger that is fluidly coupled to a Xylene isomerization reactor outlet stream before a separator drum, and is fluidly coupled to the first heating fluid circuit, and a second para-xylene separation-xylene isomerization reaction and separation unit heat source comprising a heat exchanger that is fluidly coupled to a de-heptanizer column overhead stream, and is fluidly coupled to the first heating fluid circuit;

a third sub-set of the first plurality of heat sources comprises an aromatics complex-benzene extraction unit heat source comprising a heat exchanger that is fluidly coupled to an overhead stream, and is fluidly coupled to the first heating fluid circuit; and a fourth sub-set of the first plurality of heat sources comprises at least four continuous catalytic cracking heat sources, comprising:
   a first continuous catalytic cracking heat source comprising a heat exchanger that is fluidly coupled to a CCR last stage reactor outlet after a feed-effluent heat exchanger stream, and is fluidly coupled to the first heating fluid circuit,
   a second continuous catalytic cracking heat source comprising a heat exchanger that is fluidly coupled to a 1st stage compressor outlet stream, and is fluidly coupled to the first heating fluid circuit,
   a third continuous catalytic cracking heat source comprising a heat exchanger that is fluidly coupled to a 2nd stage compressor outlet stream, and is fluidly coupled to the first heating fluid circuit, and
   a fourth continuous catalytic cracking heat source comprising a heat exchanger that is fluidly coupled to a CCR light reformate splitter column overhead stream, and is fluidly coupled to the first heating fluid circuit.

19. The method of claim 18, wherein a first sub-set of the second plurality of heat sources comprises at least three para-xylene separation unit heat sources, comprising:
   a first para-xylene separation unit heat source comprising a heat exchanger that is fluidly coupled to an extract column overhead stream, and is fluidly coupled to the second heating fluid circuit,
   a second para-xylene separation unit heat source comprising a heat exchanger that is fluidly coupled to a Raffinate column overhead stream, and is fluidly coupled to the second heating fluid circuit, and
   a third para-xylene separation unit heat source comprising a heat exchanger that is fluidly coupled to a heavy Raffinate splitter column overhead stream, and is fluidly coupled to the second heating fluid circuit.

20. The method of claim 19, wherein
a first sub-set of the third plurality of heat sources comprises at least three diesel hydrotreating reaction and stripping heat sources, comprising:
   a first diesel hydrotreating reaction and stripping heat source comprising a heat exchanger that is fluidly coupled to a light effluent to cold separator stream, and is fluidly coupled to the third heating fluid circuit,
   a second diesel hydrotreating reaction and stripping heat source comprising a heat exchanger that is fluidly coupled to a diesel stripper overhead stream, and is fluidly coupled to the third heating fluid circuit,
   a third diesel hydrotreating reaction and stripping heat source comprising a heat exchanger that is fluidly coupled to a diesel stripper product stream, and is fluidly coupled to the third heating fluid circuit; and
a second sub-set of the third plurality of heat sources comprises at least seven hydrocracking plant heat sources, comprising:
   a first hydrocracking plant heat source comprising a heat exchanger that is fluidly coupled to a 2nd reaction section 2nd stage cold high pressure separator feed stream, and is fluidly coupled to the third heating fluid circuit,
   a second hydrocracking plant heat source comprising a heat exchanger that is fluidly coupled to a 1st reaction section 1st stage cold high pressure separator feed stream, and is fluidly coupled to the third heating fluid circuit,
   a third hydrocracking plant heat source comprising a heat exchanger that is fluidly coupled to a product stripper overhead stream, and is fluidly coupled to the third heating fluid circuit,
   a fourth hydrocracking plant heat source comprising a heat exchanger that is fluidly coupled to a main fractionator overhead stream, and is fluidly coupled to the third heating fluid circuit,
   a fifth hydrocracking plant heat source comprising a heat exchanger that is fluidly coupled to a kerosene product stream, and is fluidly coupled to the third heating fluid circuit,
   a sixth hydrocracking plant heat source comprising a heat exchanger that is fluidly coupled to a kerosene pumparound stream, and is fluidly coupled to the third heating fluid circuit, and
   a seventh hydrocracking plant heat source comprises a heat exchanger that is fluidly coupled to a diesel product stream, and is fluidly coupled to the third heating fluid circuit.

21. A method of recovering heat energy generated by a petrochemical refining system, the method comprising:
   identifying, in a geographic layout, a first heating fluid circuit thermally coupled to a first plurality of heat sources from a first plurality of sub-units of a petrochemical refining system, the first plurality of sub-units comprising a continuous catalytic reforming (CCR) and aromatics refining system;
   identifying, in the geographic layout, a second heating fluid circuit thermally coupled to a second plurality of heat sources from a second plurality of sub-units of the petrochemical refining system, the second plurality of sub-units comprising the CCR and aromatics refining system;
   identifying, in the geographic layout, a third heating fluid circuit thermally coupled to a third plurality of heat sources of a third plurality of sub-units of the petrochemical refining system, the third plurality of sub-units comprising a hydrocracking-diesel hydrotreating system;
   identifying, in a geographic layout, a first power generation system that comprises:
      a first organic Rankine cycle (ORC), the first ORC comprising (i) a first working fluid that is thermally coupled to the first and second heating fluid circuits to heat the first working fluid with the first and second heating fluids, and (ii) a first expander configured to generate electrical power from the heated first working fluid; and
      a control system configured to actuate: a first set of control valves to selectively thermally couple the first heating fluid circuit to at least a portion of the first plurality of heat sources, and a second set of control valves to selectively thermally couple the second heating fluid circuit to at least a portion of the second plurality of heat sources;
   identifying, in a geographic layout, a second power generation system that comprises:
      a second ORC, the second ORC comprising (i) a second working fluid that is thermally coupled to the second heating fluid circuit to heat the second working fluid with the third heating fluid, and (ii) a second expander configured to generate electrical power from the heated second working fluid; and a control system configured to actuate a third set of control valves to selectively thermally couple the second heating fluid circuit to at least a portion of the third plurality of heat sources; and identifying, in the geographic layout, a power generation system location to position the power generation system, wherein a heat energy recovery efficiency at the power generation system location is greater than a heat energy recovery efficiency at other locations in the geographic layout.

22. The method of claim 21, further comprising constructing the petrochemical refining system according to the geographic layout by positioning the plurality of sub-units at the plurality of sub-unit locations, positioning the power generation system at the power generation system location, interconnecting the plurality of sub-units with each other such that the interconnected plurality of sub-units are configured to refine petrochemicals, and interconnecting the power generation system with the sub-units in the first subset such that the power generation system is configured to recover heat energy from the sub-units in the first subset and to provide the recovered heat energy to the power generation system, the power generation system configured to generate power using the recovered heat energy.

23. The method of claim 21, further comprising:
operating the petrochemical refining system to refine petrochemicals; and
operating the power generation system to:
    recover heat energy from the sub-units in the first subset through the first heating fluid circuit and the second heating fluid circuit;
    provide the recovered heat energy to the power generation system; and
    generate power using the recovered heat energy.

24. The method of claim 21, further comprising operating the power generation system to generate about 45 MW of power.

* * * * *